(12) United States Patent
Martin et al.

(10) Patent No.: US 6,730,674 B2
(45) Date of Patent: May 4, 2004

(54) SULFONYL PYRIDAZINONE COMPOUNDS USEFUL AS ALDOSE REDUCTASE INHIBITORS

(75) Inventors: William H. Martin, Essex, CT (US); Banavara L. Mylari, Waterford, CT (US)

(73) Assignee: Pfizer Inc, New York, NY (US)

( * ) Notice: Subject to any disclaimer, the term of this patent is extended or adjusted under 35 U.S.C. 154(b) by 38 days.

(21) Appl. No.: 10/085,609

(22) Filed: Feb. 26, 2002

(65) Prior Publication Data

US 2003/0004139 A1 Jan. 2, 2003

Related U.S. Application Data

(60) Provisional application No. 60/272,254, filed on Feb. 28, 2001.

(51) Int. Cl.[7] ................. C07D 238/16; A61K 31/50; A61P 3/10
(52) U.S. Cl. ................. 514/247; 544/240
(58) Field of Search ................. 514/247; 544/240

(56) References Cited

U.S. PATENT DOCUMENTS

| | | | |
|---|---|---|---|
| 4,251,528 A | 2/1981 | Brittain et al. | 424/250 |
| 4,939,140 A | 7/1990 | Larson et al. | 514/222 |
| 4,996,204 A | 2/1991 | Mylari et al. | 514/248 |
| 6,218,409 B1 | 4/2001 | Ikeda | 514/342 |

FOREIGN PATENT DOCUMENTS

| | | | |
|---|---|---|---|
| FR | 2647676 | 6/1989 | A61K/31/50 |
| WO | WO9217446 | 10/1992 | |

OTHER PUBLICATIONS

Turck, et al., J. Heterocyclic Chem. 34, pp. 621–627 1997, (XP–001069540).
XP–002197229.
XP–002197230.

Primary Examiner—Mukund J. Shah
Assistant Examiner—Thomas C. McKenzie
(74) Attorney, Agent, or Firm—Peter C. Richardson; Gregg C. Benson; William F. Mulholland

(57) ABSTRACT

This invention relates to novel sulfonyl pyridazinone compounds of the formula:

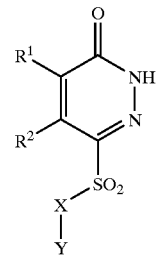

wherein $R^1$, $R^2$, X, and Y are defined herein, which are useful as aldose reductase inhibitors in the treatment or prevention of certain complications arising from diabetes mellitus, pharmaceutical compositions comprising the sulfonyl pyridazinone, pharmaceutical compositions comprising a combination of the sulfonyl pyridazinone together with a second pharmaceutical agent, therapeutic methods comprising the administration of the sulfonyl pyridazinone compounds, therapeutic methods comprising the administration of the sulfonyl pyridazinone compounds in combination with a second pharmaceutical agent and compounds useful as intermediates for preparing the sulfonyl pyridazinone compounds of this invention.

56 Claims, No Drawings

SULFONYL PYRIDAZINONE COMPOUNDS USEFUL AS ALDOSE REDUCTASE INHIBITORS

CROSS REFERENCE TO RELATED APPLICATION

This application claims the benefit of U.S. Provisional Application No. 60/272,254 filed Feb. 28, 2001.

FIELD OF THE INVENTION

This invention relates to novel sulfonyl pyridazinone compounds useful as aldose reductase inhibitors in the treatment or prevention of certain complications arising from diabetes mellitus, pharmaceutical compositions comprising the sulfonyl pyridazinone compounds, pharmaceutical compositions comprising a combination of the sulfonyl pyridazinone compounds together with a second pharmaceutical agent, therapeutic methods comprising the administration of the sulfonyl pyridazinone compounds to a mammal and therapeutic methods comprising the administration of the sulfonyl pyridazinone compounds in combination with a second pharmaceutical agent to a mammal. The invention also relates to novel compounds useful as intermediates for preparing the sulfonyl pyridazinone compounds of this invention.

BACKGROUND OF THE INVENTION

The enzyme aldose reductase is involved in regulating the reduction of aldoses, such as glucose and galactose, to their corresponding polyols, such as sorbitol and galactitol. Sulfonyl pyridazinone compounds of formula I of this invention are useful as aldose reductase inhibitors in the treatment and prevention of diabetic complications of humans and other mammals associated with increased polyol levels in certain tissues (e.g., nerve, kidney, lens and retina tissue) of affected humans and other mammals.

French Patent Publication No. 2647676 discloses pyridazinone derivatives having substituted benzyl side chains and benzothiazole side chains as being inhibitors of aldose reductase.

U.S. Pat. No. 4,251,528 discloses various aromatic carbocyclic oxophthalazinyl acetic acid compounds, as possessing aldose reductase inhibitory properties.

Commonly assigned U.S. Pat. No. 4,939,140 discloses heterocyclic oxophthalazinyl acetic acid compounds.

Commonly assigned U.S. Pat. No. 4,996,204 discloses pyridopyridazinone acetic acid compounds useful as aldose reductase inhibitors.

U.S. Pat. No. 6,218,409 discloses pharmaceutical compositions comprising an insulin sensitivity enhancer in combination with one or more anti-diabetics, including aldose reductase inhibitors.

SUMMARY OF THE INVENTION

One aspect of this invention is compounds of formula I

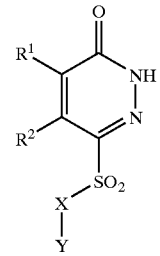

I prodrugs thereof or pharmaceutically acceptable salts of said compounds or said prodrugs,
wherein,
$R^1$ and $R^2$ are independently hydrogen or methyl,
X is a covalent bond, $NR^3$ or $CHR^4$, wherein,
  $R^3$ is $(C_1-C_3)$alkyl or a phenyl that is optionally substituted with one or more substituents selected from OH, F, Cl, Br, I, CN, $CF_3$, $(C_1-C_6)$alkyl, O—$(C_1-C_6)$alkyl, $S(O)_n$—$(C_1-C_6)$alkyl and $SO_2$—$NR^6R^7$, and $R^4$ is hydrogen or methyl, and
  Y is a phenyl or naphthyl ring optionally substituted with one or more substituents selected from Ar, OH, F, Cl, Br, I, CN, $CF_3$, $(C_1-C_6)$alkyl, O—$(C_1-C_6)$alkyl, $S(O)_n$—$(C_1-C_6)$alkyl and $SO_2$—$NR^6R^7$, or
  X and Y together are $CH_2$—CH(OH)—Ar or $CH_2$—C(O)—Ar,
wherein,
Ar is a phenyl or naphthyl ring optionally substituted with one or more substituents selected from F, Cl, Br, I, CN, $CF_3$, $(C_1-C_6)$alkyl, O—$(C_1-C_6)$alkyl, $S(O)_n$—$(C_1-C_6)$alkyl and $SO_2$—$NR^6R^7$,
n is independently for each occurrence 0, 1 or 2,
$R^6$ is independently for each occurrence H, $(C_1-C_6)$alkyl, phenyl or naphthyl, and
$R^7$ is independently for each occurrence $(C_1-C_6)$alkyl, phenyl or naphthyl,
with provisos that:
when X is a covalent bond, $R^1$ is hydrogen and $R^2$ is hydrogen, then Y is not an unsubstituted phenyl ring and Y is not a phenyl ring that is mono-substituted at the 4 position with methyl; and
when X is $CHR^4$, $R^4$ is H, $R^1$ is hydrogen and $R^2$ is hydrogen, then Y is not an unsubstituted phenyl ring.

Another aspect of this invention is pharmaceutical compositions comprising a compound of formula I

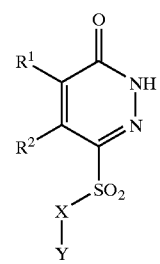

I wherein,
$R^1$ and $R^2$ are independently hydrogen or methyl,
X is a covalent bond, $NR^3$ or $CHR^4$, wherein,
  $R^3$ is $(C_1-C_3)$alkyl or a phenyl that is optionally substituted with one or more substituents selected from OH, F, Cl, Br, I, CN, $CF_3$, $(C_1-C_6)$alkyl, O—$(C_1-C_6)$alkyl, $S(O)_n$—$(C_1-C_6)$alkyl and $SO_2$—$NR^6R^7$, and $R^4$ is hydrogen or methyl, and Y is a phenyl or naphthyl ring optionally substituted with one or more substituents selected from Ar, OH, F, Cl, Br, I, CN, $CF_3$, $(C_1-C_6)$alkyl, O—$(C_1-C_6)$alkyl, $S(O)_n$—$(C_1-C_6)$alkyl and $SO_2$—$NR^6R^7$, or X and Y together are $CH_2$—CH(OH)—Ar or $CH_2$—C(O)—Ar, wherein, Ar is a phenyl or naphthyl ring optionally substituted with one or more substituents selected from F, Cl, Br, I, CN, $CF_3$, $(C_1-C_6)$alkyl, O—$(C_1-C_6)$alkyl, $S(O)_n$—$(C_1-C_6)$alkyl and $SO_2$—$NR^6R^7$, n is independently for each occurrence 0, 1 or 2, $R^6$ is independently for each occurrence H, $(C_1-C_6)$alkyl, phenyl or naphthyl, and $R^7$ is independently for each occurrence $(C_1-C_6)$alkyl, phenyl or naphthyl, a prodrug of said compound and pharmaceutically acceptable salt of said compound or said prodrug, and a pharmaceutically acceptable vehicle, diluent or carrier.

An additional aspect of this invention is pharmaceutical compositions comprising a first compound of formula I

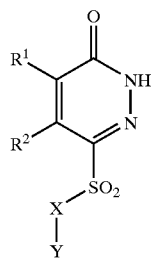

wherein, $R^1$ and $R^2$ are independently hydrogen or methyl,

X is a covalent bond, $NR^3$ or $CHR^4$, wherein, $R^3$ is $(C_1-C_3)$alkyl or a phenyl that is optionally substituted with one or more substituents selected from OH, F, Cl, Br, I, CN, $CF_3$, $(C_1-C_6)$alkyl, O—$(C_1-C_6)$alkyl, $S(O)_n$—$(C_1-C_6)$alkyl and $SO_2$—$NR^6R^7$, and $R^4$ is hydrogen or methyl, and Y is a phenyl or naphthyl ring optionally substituted with one or more substituents selected from Ar, OH, F, Cl, Br, I, CN, $CF_3$, $(C_1-C_6)$alkyl, O—$(C_1-C_6)$alkyl, $S(O)_n$—$(C_1-C_6)$alkyl and $SO_2$—$NR^6R^7$, or X and Y together are $CH_2$—CH(OH)—Ar or $CH_2$—C(O)—Ar, wherein, Ar is a phenyl or naphthyl ring optionally substituted with one or more substituents selected from F, Cl, Br, I, CN, $CF_3$, $(C_1-C_6)$alkyl, O—$(C_1-C_6)$alkyl, $S(O)_n$—$(C_1-C_6)$alkyl and $SO_2$—$NR^6R^7$, n is independently for each occurrence 0, 1 or 2, $R^6$ is independently for each occurrence H, $(C_1-C_6)$alkyl, phenyl or naphthyl, and $R^7$ is independently for each occurrence $(C_1-C_6)$alkyl, phenyl or naphthyl, a prodrug of said first compound and a pharmaceutically acceptable salt of said first compound or said prodrug, and a second compound selected from:

a sorbitol dehydrogenase inhibitor;
a selective serotonin reuptake inhibitor;
a 3-hydroxy-3-methylglutaryl coenzyme A reductase inhibitor;
an angiotensin converting enzyme inhibitor;
a glycogen phosphorylase inhibitor;
an angiotensin II receptor antagonist;
a γ-aminobutyric acid (GABA) agonist;
a phosphodiesterase type 5 inhibitor, a prodrug of said second compound and a pharmaceutically acceptable salt of said second compound or said prodrug.

A further aspect of this invention is kits comprising:

a first dosage form comprising a compound of formula I

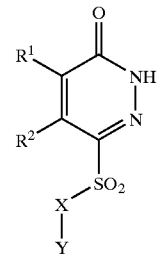

wherein, $R^1$ and $R^2$ are independently hydrogen or methyl,

X is a covalent bond, $NR^3$ or $CHR^4$, wherein, $R^3$ is $(C_1-C_3)$alkyl or a phenyl that is optionally substituted with one or more substituents selected from OH, F, Cl, Br, 1, CN, $CF_3$, $(C_1-C_6)$alkyl, O—$(C_1-C_6)$alkyl, $S(O)_n$—$(C_1-C_6)$alkyl and $SO_2$—$NR^6R^7$, and $R^4$ is hydrogen or methyl, and Y is a phenyl or naphthyl ring optionally substituted with one or more substituents selected from Ar, OH, F, Cl, Br, 1, CN, $CF_3$, $(C_1-C_6)$alkyl, O—$(C_1-C_6)$alkyl, $S(O)_n$—$(C_1-C_6)$alkyl and $SO_2$—$NR^6R^7$, or X and Y together are $CH_2$—CH(OH)—Ar or $CH_2$—C(O)—Ar, wherein, Ar is a phenyl or naphthyl ring optionally substituted with one or more substituents selected from F, Cl, Br, 1, CN, $CF_3$, $(C_1-C_6)$alkyl, O—$(C_1-C_6)$alkyl, $S(O)_n$—$(C_1-C_6)$alkyl and $SO_2$—$NR^6R^7$, n is independently for each occurrence 0, 1 or 2, $R^6$ is independently for each occurrence H, $(C_1-C_6)$alkyl, phenyl or naphthyl, and $R^7$ is independently for each occurrence $(C_1-C_6)$alkyl, phenyl or naphthyl, a prodrug thereof or a pharmaceutically acceptable salt of said compound or said prodrug;

a second dosage form comprising a second compound selected from:

a sorbitol dehydrogenase inhibitor;
a selective serotonin reuptake inhibitor;
a 3-hydroxy-3-methylglutaryl coenzyme A reductase inhibitor;
an angiotensin converting enzyme inhibitor;
a glycogen phosphorylase inhibitor;
an angiotensin II receptor antagonist;
a γ-aminobutyric acid (GABA) agonist;
a phosphodiesterase type 5 inhibitor, a prodrug thereof and a pharmaceutically acceptable salt of said compound or said prodrug; and a container.

Another aspect of this invention is therapeutic methods comprising administering to a mammal, preferably a human, in need of treatment or prevention of diabetic complications, an aldose reductase inhibiting amount of a compound of formula I

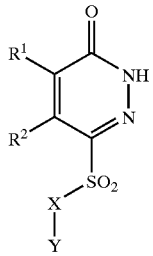

wherein,
$R^1$ and $R^2$ are independently hydrogen or methyl,
X is a covalent bond, $NR^3$ or $CHR^4$, wherein,
  $R^3$ is $(C_1-C_3)$alkyl or a phenyl that is optionally substituted with one or more substituents selected from OH, F, Cl, Br, I, CN, $CF_3$, $(C_1-C_6)$alkyl, O—$(C_1-C_6)$alkyl, $S(O)_n$—$(C_1-C_6)$alkyl and $SO_2$—$NR^6R^7$, and $R^4$ is hydrogen or methyl, and
Y is a phenyl or naphthyl ring optionally substituted with one or more substituents selected from Ar, OH, F, Cl, Br, I, CN, $CF_3$, $(C_1-C_6)$alkyl, O—$(C_1-C_6)$alkyl, $S(O)_n$—$(C_1-C_6)$alkyl and $SO_2$—$NR^6R^7$, or
X and Y together are $CH_2$—CH(OH)—Ar or $CH_2$—C(O)—Ar,
wherein,
Ar is a phenyl or naphthyl ring optionally substituted with one or more substituents selected from F, Cl, Br, I, CN, $CF_3$, $(C_1-C_6)$alkyl, O—$(C_1-C_6)$alkyl, $S(O)_n$—$(C_1-C_6)$alkyl and $SO_2$—$NR^6R^7$,
n is independently for each occurrence 0, 1 or 2,
$R^6$ is independently for each occurrence H, $(C_1-C_6)$alkyl, phenyl or naphthyl, and
$R^7$ is independently for each occurrence $(C_1-C_6)$alkyl, phenyl or naphthyl,
a prodrug of said compound or a pharmaceutically acceptable salt of said compound or said prodrug.

An additional aspect of this invention is a therapeutic method comprising administering to a mammal in need of treatment or prevention of diabetic complications an aldose reductase inhibiting amount of a first compound of formula I

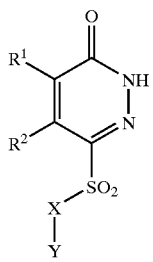

wherein,
$R^1$ and $R^2$ are independently hydrogen or methyl,
X is a covalent bond, $NR^3$ or $CHR^4$, wherein,
  $R^3$ is $(C_1-C_3)$alkyl or a phenyl that is optionally substituted with one or more substituents selected from OH, F, Cl, Br, I, CN, $CF_3$, $(C_1-C_6)$alkyl, O—$(C_1-C_6)$alkyl, $S(O)_n$—$(C_1-C_6)$alkyl and $SO_2$—$NR^6R^7$, and $R^4$ is hydrogen or methyl, and
Y is a phenyl or naphthyl ring optionally substituted with one or more substituents selected from Ar, OH, F, Cl, Br, I, CN, $CF_3$, $(C_1-C_6)$alkyl, O—$(C_1-C_6)$alkyl, $S(O)_n$—$(C_1-C_6)$alkyl and $SO_2$—$NR^6R^7$, or
X and Y together are $CH_2$—CH(OH)—Ar or $CH_2$—C(O)—Ar,
wherein,
Ar is a phenyl or naphthyl ring optionally substituted with one or more substituents selected from F, Cl, Br, I, CN, $CF_3$, $(C_1-C_6)$alkyl, O—$(C_1-C_6)$alkyl, $S(O)_n$—$(C_1-C_6)$alkyl and $SO_2$—$NR^6R^7$,
n is independently for each occurrence 0, 1 or 2,
$R^6$ is independently for each occurrence H, $(C_1-C_6)$alkyl, phenyl or naphthyl, and
$R^7$ is independently for each occurrence $(C_1-C_6)$alkyl, phenyl or naphthyl,
a prodrug of said first compound or a pharmaceutically acceptable salt of said first compound or said prodrug, and
a second compound selected from:
  a sorbitol dehydrogenase inhibitor;
  a selective serotonin reuptake inhibitor;
  a 3-hydroxy-3-methylglutaryl coenzyme A reductase inhibitor;
  an angiotensin converting enzyme inhibitor;
  a glycogen phosphorylase inhibitor;
  an angiotensin II receptor antagonist;
  a γ-aminobutyric acid (GABA) agonist;
  a phosphodiesterase type 5 inhibitor,
a prodrug of said second compound and a pharmaceutically acceptable salt of said compound or said prodrug.

In a preferred embodiment of the compound of formula I, composition and kit aspects of this invention, X is a covalent bond.

In another preferred embodiment of the compound of formula I, composition and kit aspects of this invention, X is $CHR^4$ wherein $R^4$ is hydrogen or methyl.

In an additional preferred embodiment of the compound of formula I, composition and kit aspects of this invention, X is $NR^3$, wherein $R^3$ is $(C_1-C_3)$alkyl or a phenyl that is optionally substituted with one or more substituents selected from OH, F, Cl, Br, I, CN, $CF_3$ $(C_1-C_6)$alkyl, O—$(C_1-C_6)$alkyl, $S(O)_n$—$(C_1-C_6)$alkyl and $SO_2$—$NR^6R^7$.

In another preferred embodiment of the compound of formula I, composition and kit aspects of this invention, $R^1$ and $R^2$ are both hydrogen.

In a preferred embodiment of the compound of formula I, composition and kit aspects of this invention wherein X is a covalent bond, Y is a phenyl or naphthyl ring optionally substituted with one or more substituents selected from Ar, OH, F, Cl, Br, I, CN, $CF_3$, $(C_1-C_6)$alkyl, and O—$(C_1-C_6)$alkyl, wherein Ar is a phenyl or naphthyl ring optionally substituted with one or more substituents selected from F, Cl, Br, I, CN, $CF_3$, $(C_1-C_6)$alkyl and O—$(C_1-C_6)$alkyl.

In a more preferred embodiment of the compound of formula I, composition and kit aspects of this invention wherein X is a covalent bond, Y is a first phenyl or naphthyl ring optionally substituted with one or more substituents selected from Ar, OH, F, Cl, Br, $CF_3$, $(C_1-C_6)$alkyl, and O—$(C_1-C_6)$alkyl, wherein Ar is a second phenyl or naphthyl ring optionally substituted with one or more substituents selected from F, Cl, Br, I, CN, $CF_3$, $(C_1-C_6)$alkyl and O—$(C_1-C_6)$alkyl, and preferably selected from F and $CF_3$, with the proviso that said first phenyl or naphthyl ring is substituted with no more than one Ar.

In an even more preferred embodiment of the compound of formula I, composition and kit aspects of this invention wherein X is a covalent bond, the compounds of formula I are preferably selected from:

6-(3-trifluoromethyl-benzenesulfonyl)-2H-pyridazin-3-one;
6-(4-bromo-2-fluoro-benzenesulfonyl)-2H-pyridazin-3-one;
6-(4-trifluoromethyl-benzenesulfonyl)-2H-pyridazin-3-one;
6-(2-bromo-benzenesulfonyl)-2H-pyridazin-3-one;
6-(3,4-dichloro-benzenesulfonyl)-2H-pyridazin-3-one;
6-(4-methoxy-benzenesulfonyl)-2H-pyridazin-3-one;
6-(3-bromo-benzenesulfonyl)-2H-pyridazin-3-one;
6-(biphenyl-4-sulfonyl)-2H-pyridazin-3-one;
6-(4'-fluoro-biphenyl-4-sulfonyl)-2H-pyridazin-3-one;
6-(4'-trifluoromethyl-biphenyl-4-sulfonyl)-2H-pyridazin-3-one;
6-(3',5'-bis-trifluoromethyl-biphenyl-4-sulfonyl)-2H-pyridazin-3-one;
6-(biphenyl-2-sulfonyl)-2H-pyridazin-3-one;
6-(4'-trifluoromethyl-biphenyl-2-sulfonyl)-2H-pyridazin-3-one;
6-(2-hydroxy-benzenesulfonyl)-2H-pyridazin-3-one;
6-(2-chloro-benzenesulfonyl)-2H-pyridazin-3-one;
6-(3-chloro-benzenesulfonyl)-2H-pyridazin-3-one;
6-(2,3-dichloro-benzenesulfonyl)-2H-pyridazin-3-one;
6-(2,5-dichloro-benzenesulfonyl)-2H-pyridazin-3-one;
6-(4-fluoro-benzenesulfonyl)-2H-pyridazin-3-one;
6-(4-chloro-benzenesulfonyl)-2H-pyridazin-3-one;
6-(2-fluoro-benzenesulfonyl)-2H-pyridazin-3-one;
6-(2,3-difluoro-benzenesulfonyl)-2H-pyridazin-3-one;
6-(2,4-dichloro-benzenesulfonyl)-2H-pyridazin-3-one;
6-(2,4-difluoro-benzenesulfonyl)-2H-pyridazin-3-one;
6-(2,6-dichloro-benzenesulfonyl)-2H-pyridazin-3-one;
6-(2-chloro-4-fluoro-benzenesulfonyl)-2H-pyridazin-3-one;
6-(2-bromo-4-fluoro-benzenesulfonyl)-2H-pyridazin-3-one; and
6-(naphthalene-1-sulfonyl)-2H-pyridazin-3-one, more preferably from:
6-(2-chloro-benzenesulfonyl)-2H-pyridazin-3-one;
6-(3-chloro-benzenesulfonyl)-2H-pyridazin-3-one;
6-(2,3-dichloro-benzenesulfonyl)-2H-pyridazin-3-one;
6-(2,5-dichloro-benzenesulfonyl)-2H-pyridazin-3-one;
6-(4-fluoro-benzenesulfonyl)-2H-pyridazin-3-one;
6-(4-chloro-benzenesulfonyl)-2H-pyridazin-3-one;
6-(2-fluoro-benzenesulfonyl)-2H-pyridazin-3-one;
6-(2,3-difluoro-benzenesulfonyl)-2H-pyridazin-3-one;
6-(2,4-dichloro-benzenesulfonyl)-2H-pyridazin-3-one;
6-(2,4-difluoro-benzenesulfonyl)-2H-pyridazin-3-one;
6-(2,6-dichloro-benzenesulfonyl)-2H-pyridazin-3-one;
6-(2-chloro-4-fluoro-benzenesulfonyl)-2H-pyridazin-3-one;
6-(2-bromo-4-fluoro-benzenesulfonyl)-2H-pyridazin-3-one; and
6-(naphthalene-1-sulfonyl)-2H-pyridazin-3-one, even more preferably from:
6-(2-chloro-benzenesulfonyl)-2H-pyridazin-3-one;
6-(3-chloro-benzenesulfonyl)-2H-pyridazin-3-one;
6-(2,3-dichloro-benzenesulfonyl)-2H-pyridazin-3-one;
6-(2,5-dichloro-benzenesulfonyl)-2H-pyridazin-3-one;
6-(2,3-difluoro-benzenesulfonyl)-2H-pyridazin-3-one;
6-(2,4-dichloro-benzenesulfonyl)-2H-pyridazin-3-one;
6-(2,4-difluoro-benzenesulfonyl)-2H-pyridazin-3-one;
6-(2,6-dichloro-benzenesulfonyl)-2H-pyridazin-3-one;
6-(2-chloro-4-fluoro-benzenesulfonyl)-2H-pyridazin-3-one;
6-(2-bromo-4-fluoro-benzenesulfonyl)-2H-pyridazin-3-one; and
6-(naphthalene-1-sulfonyl)-2H-pyridazin-3-one, and
especially more preferably from:
6-(2,3-difluoro-benzenesulfonyl)-2H-pyridazin-3-one;
6-(2,4-dichloro-benzenesulfonyl)-2H-pyridazin-3-one;
6-(2-bromo-4-fluoro-benzenesulfonyl)-2H-pyridazin-3-one; and
6-(naphthalene-1-sulfonyl)-2H-pyridazin-3-one.

In a preferred embodiment of the compound of formula I, composition and kit aspects of this invention wherein X is $CHR^4$ wherein $R^4$ is hydrogen or methyl, Y is a phenyl or naphthyl ring optionally substituted with one or more substituents selected from Ar, OH, F, Cl, Br, I, CN, $CF_3$, $(C_1-C_6)$alkyl, and O—$(C_1-C_6)$alkyl, wherein Ar is a phenyl or naphthyl ring optionally substituted with one or more substituents selected from F, Cl, Br, I, CN, $CF_3$ $(C_1-C_6)$alkyl and O—$(C_1-C_8)$alkyl.

In an even more preferred embodiment of the compound of formula I, composition and kit aspects of this invention wherein X is $CHR^4$ wherein $R^4$ is hydrogen or methyl, Y is a phenyl or naphthyl ring optionally substituted with one or more substituents selected from F, Cl, Br, $CF_3$, $(C_1-C_6)$alkyl, and O—$(C_1-C_6)$alkyl.

In an especially more preferred embodiment of the compound of formula I, composition and kit aspects of this invention wherein X is $CHR^4$ wherein $R^4$ is hydrogen or methyl, the compounds of formula I are selected from:

6-(4-bromo-2-fluoro-phenylmethanesulfonyl)-2H-pyridazin-3-one;
6-(2,6-dichloro-phenylmethanesulfonyl)-2H-pyridazin-3-one;
6-(3-chloro-5-methyl-phenylmethanesulfonyl)-2H-pyridazin-3-one;
6-(3,4-dimethoxy-phenylmethanesulfonyl)-2H-pyridazin-3-one;
6-(2,5-dimethoxy-phenylmethanesulfonyl)-2H-pyridazin-3-one;
6-(3,5-dichloro-phenylmethanesulfonyl)-2H-pyridazin-3-one;
6-(2-methoxy-phenylmethanesulfonyl)-2H-pyridazin-3-one;
6-(3,4-dimethyl-phenylmethanesulfonyl)-2H-pyridazin-3-one;
6-(naphthalen-2-yl-methanesulfonyl)-2H-pyridazin-3-one;
6-(3,5-dichloro-2-methyl-phenylmethanesulfonyl)-2H-pyridazin-3-one;
6-(2-chloro-4,6-difluoro-phenylmethanesulfonyl)-2H-pyridazin-3-one;
6-(2-chloro-3-methyl-phenylmethanesulfonyl)-2H-pyridazin-3-one;

6-(4-bromo-2-fluoro-phenylmethanesulfonyl)-2H-pyridazin-3-one;

6-(2-chloro-phenylmethanesulfonyl)-2H-pyridazin-3-one;

6-(2-fluoro-phenylmethanesulfonyl)-2H-pyridazin-3-one;

6-(2,4-difluoro-phenylmethanesulfonyl)-2H-pyridazin-3-one;

6-(4-chloro-2-fluoro-phenylmethanesulfonyl)-2H-pyridazin-3-one;

6-(2,3,4-trifluoro-phenylmethanesulfonyl)-2H-pyridazin-3-one;

6-(2,4,6-trifluoro-phenylmethanesulfonyl)-2H-pyridazin-3-one;

6-(2-fluoro-3-methyl-phenylmethanesulfonyl)-2H-pyridazin-3-one;

6-(3-difluoromethyl-phenylmethanesulfonyl)-2H-pyridazin-3-one;

6-(2,3-dichloro-phenylmethanesulfonyl)-2H-pyridazin-3-one;

6-(2-trifluoromethyl-phenylmethanesulfonyl)-2H-pyridazin-3-one;

6-(2-fluoro-3-trifluoromethyl-phenylmethanesulfonyl)-2H-pyridazin-3-one;

6-(2-chloro-6-fluoro-phenylmethanesulfonyl)-2H-pyridazin-3-one;

6-(2-methoxy-phenylmethanesulfonyl)-2H-pyridazin-3-one;

6-(2,3-dichloro-phenylmethanesulfonyl)-2H-pyridazin-3-one;

6-(1-phenyl-ethanesulfonyl)-2H-pyridazin-3-one;

6-[1-(3-trifluoromethyl-phenyl)-ethanesulfonyl]-2H-pyridazin-3-one;

6-[1-(2-trifluoromethyl-phenyl)-ethanesulfonyl]-2H-pyridazin-3-one; and

6-[1-(2,4-dichloro-phenyl)-ethanesulfonyl]-2H-pyridazin-3-one.

In a preferred embodiment of the compound of formula I, composition and kit aspects of this invention wherein X is $NR^3$, wherein $R^3$ is as defined above, Y is a phenyl or naphthyl ring optionally substituted with one or more substituents selected from Ar, OH, F, Cl, Br, I, CN, $CF_3$, $(C_1-C_6)$alkyl, and O—$(C_1-C_6)$alkyl, wherein Ar is a phenyl or naphthyl ring optionally substituted with one or more substituents selected from F, Cl, Br, I, CN, $CF_3$ $(C_1-C_6)$alkyl and O—$(C_1-C_6)$alkyl.

In a more preferred embodiment of the compound of formula I, composition and kit aspects of this invention wherein X is $NR^3$, wherein $R^3$ is as defined above, the compound of formula I is selected from:

6-oxo-1,6-dihydro-pyridazine-3-sulfonic acid methyl-phenyl-amide;

6-oxo-1,6-dihydro-pyridazine-3-sulfonic acid isopropyl-phenyl-amide; and 6-oxo-1,6-dihydro-pyridazine-3-sulfonic acid (3,4-dichloro-phenyl)-methyl-amide.

In a preferred embodiment of the compound of formula I, composition and kit aspects of the invention, X and Y together are $CH_2$—CH(OH)—Ar or $CH_2$—C(O)—Ar, $R^1$ and $R^2$ are both hydrogen.

In a more preferred embodiment of the compound of formula I, composition and kit aspects of the invention, X and Y together are $CH_2$—CH(OH)—Ar" or $CH_2$—C(O)—Ar", $R^1$ and $R^2$ are both hydrogen, wherein Ar" is 4-chlorophenyl.

In a preferred embodiment of the pharmaceutical composition, kit and therapeutic methods aspect of this invention, said compound of formula I, a prodrug thereof or a pharmaceutically acceptable salt of said compound or said prodrug, is of an amount effective in inhibiting the enzyme aldose reductase in a mammal, preferably a human, affected by diabetes.

In a preferred embodiment of the composition aspect of this invention wherein a composition comprises a first compound of formula I, a prodrug of said first compound or a pharmaceutically acceptable salt of said first compound or said prodrug, and a second compound, a prodrug thereof or a pharmaceutically acceptable salt of said second compound or said prodrug, the compositions further comprise a pharmaceutically acceptable vehicle, diluent or carrier.

The term "combination aspects of this invention" as used herein means, any and/or all of the following: the composition aspect of this invention wherein a composition comprises a first compound of formula I, a prodrug of said first compound or a pharmaceutically acceptable salt of said first compound or said prodrug, and a second compound, a prodrug thereof or a pharmaceutically acceptable salt of said second compound or said prodrug; the kit aspects of this invention; and, the therapeutic method aspect of this invention wherein the methods comprise administering a first compound of formula I, a prodrug of said first compound or a pharmaceutically acceptable salt of said first compound or said prodrug, and a second compound, a prodrug thereof or a pharmaceutically acceptable salt of said second compound or said prodrug.

In a preferred embodiment of the combination aspects of this invention, the second compound comprises a sorbitol dehydrogenase inhibitor, preferably in a sorbitol dehydrogenase inhibiting amount.

In a further preferred embodiment of the combination aspects of this invention, the second compound comprises a selective serotonin reuptake inhibitor, preferably in a selective serotonin reuptake inhibiting amount.

In a further preferred embodiment of the combination aspects of this invention, the second compound comprises a 3-hydroxy-3-methylglutaryl coenzyme A reductase inhibitor, preferably in a 3-hydroxy-3-methylglutaryl coenzyme A reductase inhibiting amount.

In another preferred embodiment of the combination aspects of this invention, the second compound comprises an angiotensin converting enzyme inhibitor, preferably in an angiotensin converting enzyme inhibiting amount.

In an additional preferred embodiment of the combination aspects of this invention, the second compound comprises a glycogen phosphorylase inhibitor, preferably in a glycogen phosphorylase inhibiting amount.

In another preferred embodiment of the combination aspects of this invention, the second compound comprises an angiotensin II receptor antagonist, preferably in an angiotensin II receptor blocking amount.

In a further preferred embodiment of the combination aspects of this invention, the second compound comprises a γ-aminobutyric acid (GABA) agonist, preferably in a γ-aminobutyric acid receptor binding amount.

In an additional preferred embodiment of the combination aspects of this invention, the second compound comprises a phosphodiesterase type 5 inhibitor, preferably in a phosphodiesterase type 5 inhibiting amount An additional aspect of this invention is compounds of formula XI

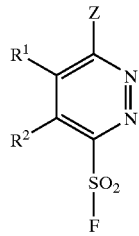

XI wherein:
R¹ and R² are independently hydrogen or methyl and Z is O—(C₁–C₆)alkyl, O—Ar', or O—CH₂—Ar', wherein Ar' is a phenyl ring that is optionally substituted with one or more substituents selected from a halogen, a (C₁–C₃)alkyl and a O—(C₁–C₃)alkyl.

In a preferred embodiment of the compound of formula XI aspects of this invention, Ar' is a phenyl ring that is optionally substituted with one or more substituents selected from Cl, Br and methyl and, more preferably, Ar' is a phenyl ring that is optionally mono- or di-substituted with Cl, Br or methyl.

In another preferred aspect of the compound of formula XI aspects of this invention R¹ and R² are both hydrogen and Z is methoxy or benzyloxy.

Another aspect of this invention is methods for preparing a compound of formula XII

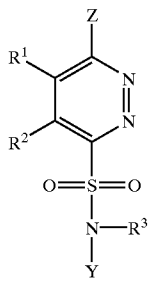

XII comprising reacting a compound of formula XI, as described above, with HN(R³)—Y to form a compound of formula XII,
wherein
Y is a phenyl or naphthyl ring optionally substituted with one or more substituents selected from Ar, OH, F, Cl, Br, I, CN, CF₃ (C₁–C₆)alkyl, O—(C₁–C₆)alkyl, S(O)ₙ—(C₁–C₆)alkyl and SO₂—NR⁶R⁷, wherein Ar is a phenyl or naphthyl ring optionally substituted with one or more substituents selected from F, Cl, Br, I, CN, CF₃, (C₁–C₆) alkyl, O—(C₁–C₆)alkyl, S(O)ₙ—(C₁–C₆)alkyl and SO₂—NR⁶R⁷, n is independently for each occurrence 0, 1 or 2, R⁶ is independently for each occurrence H, (C₁–C₆)alkyl, phenyl or naphthyl, and
R⁷ is independently for each occurrence (C₁–C₆)alkyl, phenyl or naphthyl;
R¹ and R² are independently hydrogen or methyl; and
R³ is (C₁–C₃)alkyl or a phenyl that is optionally substituted with one or more substituents selected from OH, F, Cl, Br, I, CN, CF₃, (C₁–C₆)alkyl, O—(C₁–C₆)alkyl, S(O)ₙ—(C₁–C₆)alkyl and SO₂—NR⁶R⁷, preferably (C₁–C₃)alkyl.

Another aspect of this invention is methods for preparing a compound of formula XIII

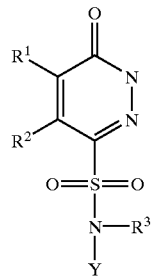

XIII comprising hydrolyzing a compound of formula XII prepared by a method of this invention with a mineral acid, preferably hydrochloric acid, to form a compound of formula XIII,
wherein:
Y is a phenyl or naphthyl ring optionally substituted with one or more substituents selected from Ar, OH, F, Cl, Br, I, CN, CF₃, (C₁–C₆)alkyl, O—(C₁–C₆)alkyl, S(O)ₙ—(C₁–C₆)alkyl and SO₂—NR⁶R⁷, wherein Ar is a phenyl or naphthyl ring optionally substituted with one or more substituents selected from F, Cl, Br, I, CN, CF₃, (C₁–C₆) alkyl, O—(C₁–C₆)alkyl, S(O)ₙ—(C₁–C₆)alkyl and SO₂—NR⁶R⁷, n is independently for each occurrence 0, 1 or 2, R⁶ is independently for each occurrence H, (C₁–C₆)alkyl, phenyl or naphthyl, and
R⁷ is independently for each occurrence (C₁–C₆)alkyl, phenyl or naphthyl;
R¹ and R² are independently hydrogen or methyl; and
R³ is (C₁–C₃)alkyl or a phenyl that is optionally substituted with one or more substituents selected from OH, F, Cl, Br, I, CN, CF₃, (C₁–C₆)alkyl, O—(C₁–C₆)alkyl, S(O)ₙ—(C₁–C₆)alkyl and SO₂—NR⁶R⁷, preferably (C₁–C₃)alkyl.

The expressions "compound(s) of formula I" and "compound(s) of this invention" as used herein, means a compound or compounds of formula I, prodrugs thereof and pharmaceutically acceptable salts of said compounds or said prodrugs. The term "compound(s)" when referring to compounds of formula I, also includes prodrugs of said compound(s) and pharmaceutically acceptable salts of said compound(s) or said prodrugs.

The term "(C₁–Cₜ)alkyl" as used herein, wherein the subscript "t" denotes an integer greater than 1, denotes a saturated monovalent straight or branched aliphatic hydrocarbon radical having one to t carbon atoms.

The expression "pharmaceutically acceptable salt" as used herein in relation to compounds of formula I of this invention includes pharmaceutically acceptable cationic salts. The expression "pharmaceutically-acceptable cationic salts" is intended to define but is not limited to such salts as the alkali metal salts, (e.g., sodium and potassium), alkaline earth metal salts (e.g., calcium and magnesium), aluminum salts, ammonium salts, and salts with organic amines such as benzathine (N,N'-dibenzylethylenediamine), choline, ethanolamine, diethanolamine, triethanolamine, ethylenediamine, meglumine (N-methylglucamine), benethamine (N-benzylphenethylamine), ethanolamine, diethylamine, piperazine, triethanolamine (2-amino-2-hydroxymethyl-1,3-propanediol) and procaine.

Pharmaceutically acceptable salts of the compounds of formula I of this invention may be readily prepared by reacting the free acid form of said compounds with an appropriate base, usually one equivalent, in a co-solvent.

Preferred co-solvents include diethylether, diglyme and acetone. Preferred bases include sodium hydroxide, sodium methoxide, sodium ethoxide, sodium hydride, potassium methoxide, magnesium hydroxide, calcium hydroxide, benzathine, choline, ethanolamine, diethanolamine, piperazine and triethanolamine. The salt is isolated by concentration to dryness or by addition of a nonsolvent. In many cases, salts may be prepared by mixing a solution of the acid with a solution of a different salt of the cation (e.g., sodium or potassium ethylhexanoate, magnesium oleate) and employing a co-solvent, as described above, from which the desired cationic salt precipitates, or can be otherwise isolated by concentration.

The term "prodrug" denotes a compound that is converted in vivo into a compound of formula I of this invention. Such compounds include N-alkyl derivatives of formula I compounds as well as O-alkyl derivatives of formula I tautomeric compounds.

The term "substituted" when used to describe a phenyl or naphthyl ring, refers to replacement of a hydrogen atom of the phenyl or naphthyl ring with another atom or group of atoms. For example, the term "mono-substituted" means that only one of the hydrogens of the phenyl or naphthyl ring has been substituted. The term "di-substituted" means that two of the hydrogens of the phenyl or naphthyl ring have been substituted.

Those skilled in the art will recognize that the compounds of this invention can exist in several tautomeric forms. All such tautomeric forms are considered as part of this invention. For example, all of the tautomeric forms of the carbonyl moiety of the compounds of formula I are included in this invention. Also, for example all enol-keto forms of compounds of formula I are included in this invention.

Those skilled in the art will also recognize that the compounds of this invention can exist in several diastereoisomeric and enantiomeric forms. All diastereoisomeric and enantiomeric forms, and racemic mixtures thereof, are included in this invention.

Those skilled in the art will further recognize that the compounds of formula I can exist in crystalline form as hydrates wherein molecules of water are incorporated within the crystal structure thereof and as solvates wherein molecules of a solvent are incorporated therein. All such hydrate and solvate forms are considered part of this invention.

This invention also includes isotopically-labeled compounds, which are identical to those described by formula I, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, sulfur, fluorine and chlorine, such as $^2$H, $^3$H, $^{13}$C, $^{14}$C, $^{15}$N, $^{18}$O, $^{17}$O, $^{31}$P, $^{32}$P, $^{35}$S, $^{18}$F and $^{36}$Cl, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically-labeled compounds of the present invention, for example those into which radioactive isotopes such as 3H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labeled compounds of formula I of this invention and prodrugs thereof can generally be prepared by carrying out the procedures disclosed in the schemes and/or in the Examples below, by substituting a readily available isotopically labeled reagent for a non-isotopically labeled reagent.

DETAILED DESCRIPTION OF THE INVENTION

In general, the compounds of formula I of this invention may be prepared by methods that include processes known in the chemical arts, particularly in light of the description contained herein. Certain processes for the manufacture of the compounds of formula I of this invention are illustrated by the following reaction schemes. Other processes are described in the experimental section. Some of the starting compounds for the reactions described in the schemes and Examples are prepared as illustrated herein. All other starting compounds may be obtained from general commercial sources, such as Sigma-Aldrich Corporation, St. Louis, Mo.

As shown in Scheme 1, compounds of this invention may be prepared by reacting dichloro pyridazine compounds of formula II or chloropyridazinone compounds of formula III with an alkali or alkali metal salt of Y—X—SO$_2$H, for example, Y—X—SO$_2$Na of formula IV, wherein R$^1$, R$^2$, X and Y are as defined herein. The reaction may be carried out in water or a mixture of water and water-miscible solvents such as dioxane or tetrahydrofuran (THF). The reaction is usually conducted at ambient pressure and at temperatures between about 80° C. and the boiling point of the solvent used.

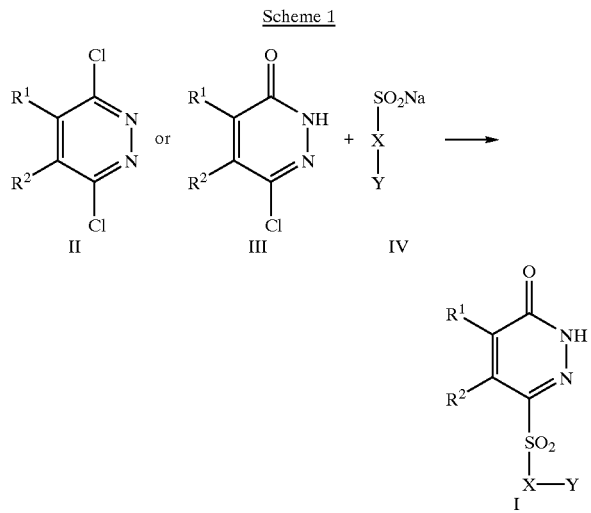

Compounds of formula I may also be prepared in accordance with the steps of Scheme 2. In step 1 of Scheme 2, a compound of formula V, wherein R$^1$, R$^2$, X and Y are as defined herein and Z is Cl, O—(C$_1$-C$_6$)alkyl, O—Ph, O—CH$_2$—Ph, wherein Ph is phenyl optionally mono- or di-substituted with chlorine, bromine, or methyl, is reacted with a thiol compound of formula VI to form the formula VII sulfenyl compound.

SCHEME 2

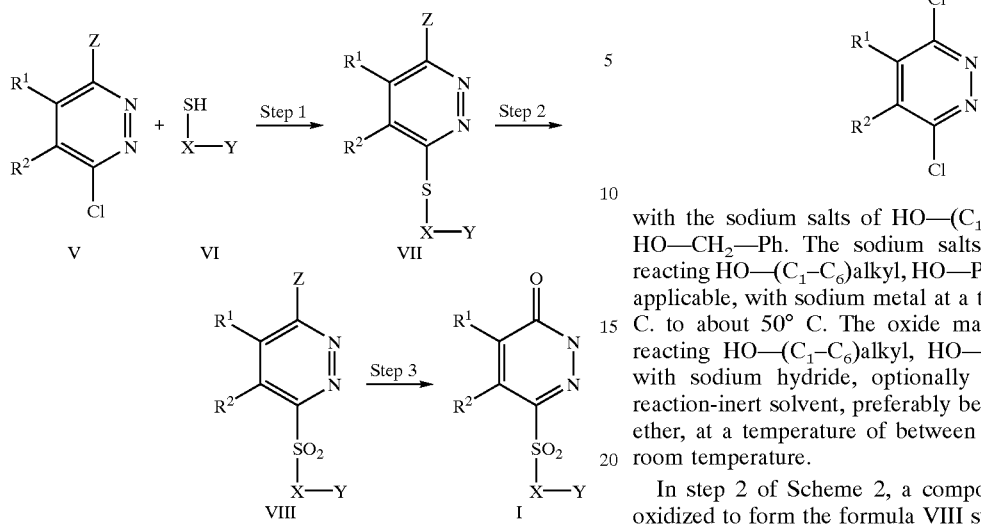

In one method of step 1 of Scheme 2, a formula V compound is reacted with the alkali metal salt of a formula VI thiol. The alkali metal salt is prepared by reacting the formula VI thiol with an alkali metal $(C_1-C_6)$alkoxide in $(C_1-C_6)$alkyl-OH. It is preferable that the $(C_1-C_6)$alkoxide and the $(C_1-C_6)$alkyl-OH correspond to Z of the formula V compound. For example, when Z is OMe the preferred alkoxide is an alkali metal methoxide, preferably sodium methoxide, and the preferred $(C_1-C_6)$alkyl-OH is methanol. Potassium t-butoxide may be used in any combination of alkanol and Z. Preferred metal oxides are sodium methoxide and sodium ethoxide. Excess alcohol from the reaction forming the alkali metal salt of the formula VI thiol compound is evaporated away and the resulting alkali metal salt is refluxed overnight in an aromatic hydrocarbon solvent, preferably toluene, together with the formula V compound to form the formula VII compound.

In another method of step 1 of Scheme 2, compounds of formula VII may be prepared by reacting compounds of formula V with compounds of formula VI in N,N-dimethylformamide (DMF) containing sodium or potassium carbonate. The reaction is preferably conducted at ambient pressure and at a temperature of between about 60° C. and about 120° C.

In a further method of step 1 of Scheme 2, compounds of formula V, wherein Z is O—$(C_1-C_6)$alkyl, are reacted with compounds of formula VI either in a polar non-aqueous solvent (e.g., acetonitrile) or in an ether solvent (e.g., diglyme, tetrahydrofuran or DMF) containing alkali or alkali earth metal hydrides, preferably sodium hydride, or potassium t-butoxide. A preferred solvent is DMF.

Compounds of formula V of Scheme 2, wherein Z is O—$(C_1-C_6)$alkyl, O—Ph, O—$CH_2$—Ph, wherein Ph is phenyl optionally mono- or di-substituted with chlorine, bromine, or methyl, may be prepared by reacting a compound of formula II

II with the sodium salts of HO—$(C_1-C_6)$alkyl, HO—Ph or HO—$CH_2$—Ph. The sodium salts may be prepared by reacting HO—$(C_1-C_6)$alkyl, HO—Ph or HO—$CH_2$—Ph, as applicable, with sodium metal at a temperature of about 0° C. to about 50° C. The oxide may also be prepared by reacting HO—$(C_1-C_6)$alkyl, HO—Ph or HO—$CH_2$—Ph with sodium hydride, optionally in the presence of a reaction-inert solvent, preferably benzene, toluene, THF or ether, at a temperature of between about 0° C. and about room temperature.

In step 2 of Scheme 2, a compound of formula VII is oxidized to form the formula VIII sulfonyl compound. The formula VII compounds may be oxidized with 30% hydrogen peroxide, optionally in the presence of formic acid, acetic acid or a peracid, such as m-chloroperbenzoic acid (MCPBA), in a halocarbon solvent (e.g., dichloromethane). The reaction is preferably conducted at ambient pressure and at a temperature of between about 20° C. and about 40° C., and is complete in about three to about six hours. The reaction should be monitored carefully to avoid over-oxidation of the nitrogen atoms to N-oxides. N-oxides that are formed may be converted to the reduced pyridazine compound by reacting the N-oxide with triethylphosphite, sodium sulfite or potassium sulfite, preferably at about 100° C. for about four hours.

The formula VIII compounds of step 3 of Scheme 2 are hydrolyzed with a mineral acid, e.g., concentrated hydrochloric acid, alone or in an ether solvents such as dioxane, to obtain the compound of formula I. The reaction of step 3 is preferably conducted at ambient pressure and at the refluxing temperature of the solvent used.

Scheme 3 provides still another method of preparing compounds of formula I. In Scheme 3, a chloropyridazinone compound of formula III is reacted with a thiol compound of formula VI to form a sulfinylpyridazinone compound of formula XI. The reaction is preferably performed in the presence of an alkali or an alkali metal alkoxide, for example potassium tertbutoxide, in reaction-inert polar solvent such as DMF or acetonitrile at about room temperature to about 100° C. The resulting compound of formula I is oxidized with hydrogen peroxide, optionally in the presence of acetic acid or a peracid, preferably m-chloroperbenzoic acid (MCPBA), in a halocarbon solvent such as dichloromethane, to form the compound of formula I.

SCHEME 3

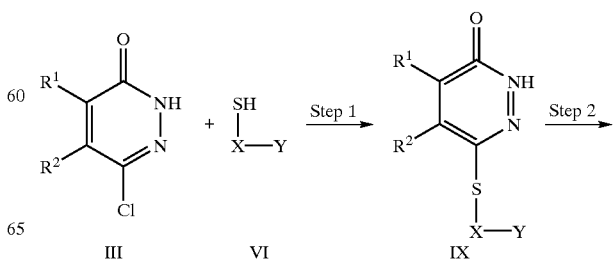

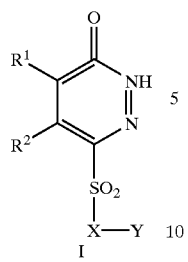

Compounds of formula I wherein X is CHR⁴, wherein R⁴ is hydrogen or methyl may be prepared according to Scheme 4. In step 1 of Scheme 4, a compound of formula X, wherein Z is Cl, O—($C_1$-$C_6$)alkyl, O—$Ph^1$, O—$CH_2$—$Ph^1$, wherein $Ph^1$ is phenyl optionally mono- or di-substituted with chlorine, bromine, or methyl, is reacted with Y—X—L, wherein L is a leaving group, preferably Cl, Br, I, $OSO_2CH_3$, $OSO_2CF_3$, or $OSO_2Ph^2$, wherein $Ph^2$ is a phenyl optionally monosubtituted with Br, Cl or $OCH_3$, in the presence of a base, preferably sodium carbonate, potassium carbonate or sodium hydride to form a compound of formula VII. When the base is sodium carbonate or potassium carbonate, the reaction solvent is preferably acetone. However, if the base is sodium hydride, DMF or acetonitrile is used as the reaction solvent. The reaction is preferably conducted at ambient pressure and at a temperature of between about room temperature and about 100° C. Steps 2 and 3 are analogous to steps 2 and 3 of Scheme 2 and are conducted in the same manner thereof.

SCHEME 4

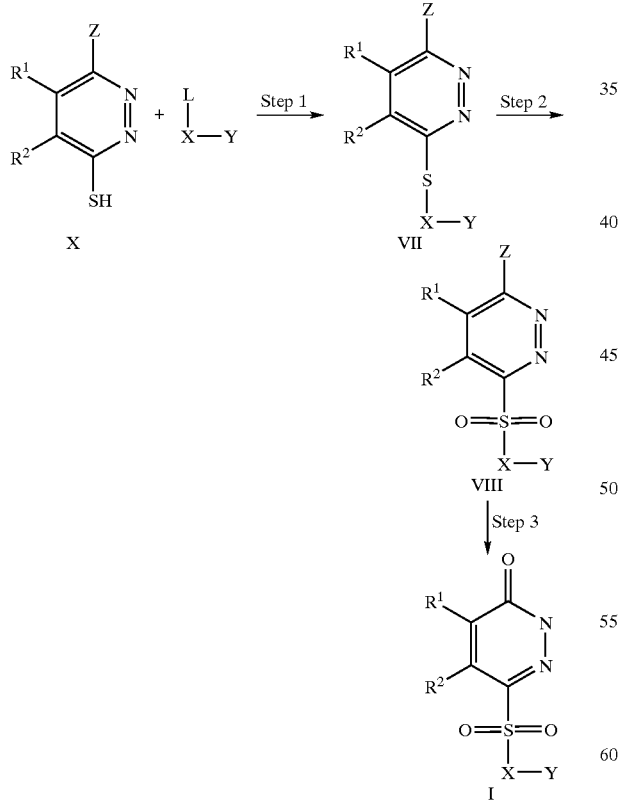

Compounds of formula I wherein X and Y together form $CH_2C(O)Ar$ may be prepared according to Scheme 4 by reacting, in step 1, compounds of formula X with $LCH_2C(O)Ar$ to form a compound of formula VII The reaction is conducted in the presence of a base, preferably sodium carbonate or potassium carbonate and in a reaction-inert solvent such as dimethyl formamide. The reaction temperature is preferably from about room temperature to about 80° C. Steps 2 and step 3 of Scheme 4 are performed in a manner analogous to steps 2 and 3 of Scheme 2.

Compounds of formula I wherein X and Y together form —$CH_2CH(OH)Ar$ may be prepared by reacting compounds of formula I wherein X and Y together form —$CH_2C(O)Ar$ with sodium borohydride in alcoholic solvents such as methanol, ethanol or isopropanol. The reaction is preferably conducted at a temperature of about 0° C. to about 60° C. and at ambient pressure.

Compounds of formula I wherein X is $NF^3$ wherein $R^3$ is ($C_1$-$C_3$)alkyl (formula XIII compounds) may be prepared in accordance with Scheme 5. In step 1 of Scheme 5, a compound of formula V, wherein Z is Cl, —O—($C_1$-$C_6$) alkyl, O—Ph, O—$CH_2$—Ph, wherein Ph is phenyl optionally mono- or di-substituted with chlorine, bromine, or methyl, is reacted with thiourea in a ketone solvents, preferably acetone, ethyl methyl ketone or isobutyl ketone, to obtain a compound of formula X. Step 1 is conducted at ambient pressure and at the refluxing temperature of the solvent. Compounds of formula V may be prepared as described above for Scheme 2.

SCHEME 5

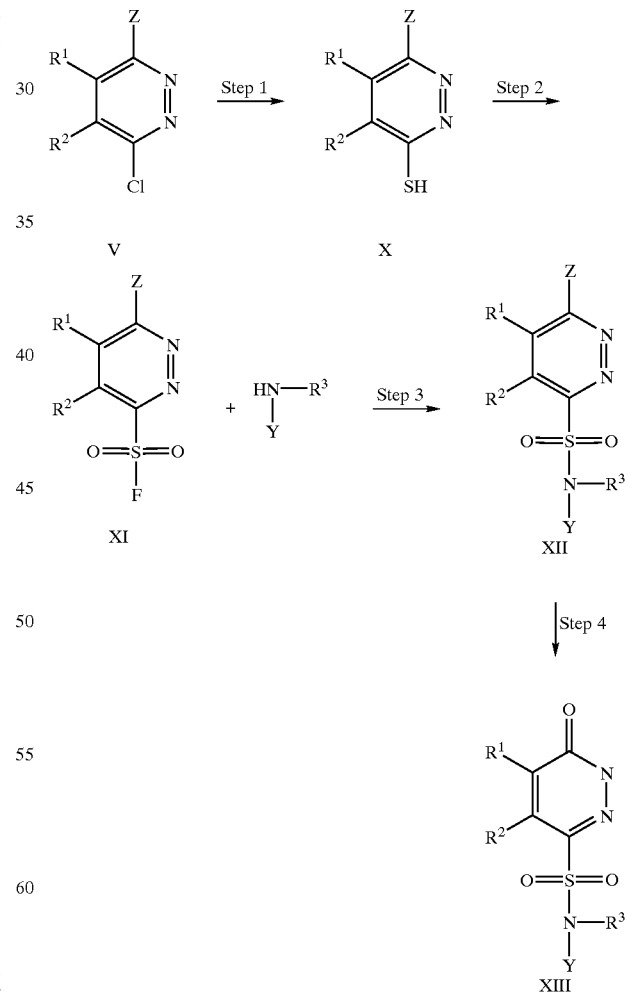

In step 2 of Scheme 5, a compound of formula XI is prepared according to the process disclosed in J. Heterocyclic Chem., 1998, 35, 429–436. Compounds of formula XI are particularly useful as intermediates in the preparation of compounds of formula I.

In Step 3 of Scheme 5, a formula XII compound is prepared by reacting a compound of formula XI with excess $HN(R^3)$—Y, optionally in an organic reaction inert base, preferably a trialkyl amine selected from trimethylamine, triethylamine, and dimethyl-isopropyl-amines, more preferably triethylamine. The reaction may optionally be performed in a reaction inert solvent such as an ether, halocarbon or aromatic hydrocarbon solvent, preferably selected from diethyl ether, isopropyl ether, tetrahydrofuran, diglyme, chloroform, methylene dichloride, benzene and toluene. The reaction of step 3 is preferably performed at a temperature of about room temperature to about the refluxing temperature of the solvent that is used.

In step 4 of Scheme 5, a compound of formula XIII may be prepared by hydrolyzing a compound of formula XII with a mineral acid such as concentrated hydrochloric acid, either alone or an ether solvent (e.g., dioxane). The reaction may be conducted at about room pressure to about the refluxing temperature of the solvent used.

Compounds of formula I wherein X is a covalent bond and Y is a phenyl or napthyl ring substituted with hydroxy may be prepared by reacting compounds of formula I wherein Y is phenyl or naphthyl substituted with $C_1$-$C_6$ alkoxy with a dealkylating reagents such as $AlCl_3$, $AlBr_3$, or $BF_3$. When $AlCl_3$ or $AlBr_3$ are the dealkylating reagent, the reaction is preferably carried out without any solvent. When the dealkylating reagent is $BF_3$, a halocarbon solvent is preferably used, preferably methylene chloride or ethylene chloride. The reaction is conducted at ambient pressure and at temperatures between about −60° C. to about 80° C.

Compounds of formula I wherein X is a covalent bond and Y is phenyl or naphthyl substituted with an optionally substituted phenyl or naphthyl ring may be prepared by first reacting compounds of formula VIII wherein X is a covalent bond, Z is O—($C_1$-$C_6$)alkyl, Y is a phenyl or napthyl that has a bromo or iodo substitutent with an appropriately substituted phenyl or naphthyl boronic acid in the presence of a palladium catalyst such as $Pd[P(Ph)_3]_4$ and in the presence of either potassium carbonate or sodium carbonate. The reaction is preferably conducted in an aromatic hydrocarbon solvent, preferably toluene, or in a $C_1$-$C_6$ alcohol, preferably ethanol, at ambient pressure and at a temperature of about room temperature to the refluxing temperature of the solvent used. The product of the first step is hydrolyzed with a mineral acid, preferably hydrochloric acid, alone or an ether solvent, preferably dioxane, to obtain a compound of formula I wherein Y is phenyl or naphthyl substituted with an optionally substituted phenyl or naphthyl ring.

The compounds of formula I of the present invention inhibit the bioconversion of glucose to sorbitol catalyzed by the enzyme aldose reductase and as such have utility in the treatment of diabetic complications including but not limited to such complications as diabetic neuropathy, diabetic nephropathy, diabetic cardiomyopathy, diabetic retinopathy, diabetic cataracts and tissue ischemia. Such aldose reductase inhibition is readily determined by those skilled in the art according to standard assays known to those skilled in the art (e.g., B. L. Mylari, et al., J. Med. Chem., 1991, 34, 108–122) and according to the protocol described in the General Experimental Procedures.

This invention also relates to therapeutic methods for treating or preventing diabetic complications in a mammal wherein a compound of formula I of this invention is administered as part of an appropriate dosage regimen designed to obtain the benefits of the therapy. The appropriate dosage regimen, the amount of each dose administered and the intervals between doses of the compound will depend upon the compound of formula I of this invention being used, the type of pharmaceutical compositions being used, the characteristics of the subject being treated and the severity of the conditions. Generally, in carrying out the methods of this invention, an effective dosage for the compounds of formula I of this invention is in the range of about 0.1 mg/kg/day to about 500 mg/kg/day in single or divided doses. However, some variation in dosage will necessarily occur depending on the condition of the subject being treated. The individual responsible for dosing will, in any event, determine the appropriate dose for the individual subject.

The standard assays used to determine aldose reductase inhibiting activity, as described above, may be used to determine dosage levels in humans and other mammals of the compounds of formula I of this invention. Such assays provide a means to compare the activities of the compounds of formula I of this invention and other known compounds that are aldose reductase inhibitors. The results of these comparisons are useful for determining such dosage levels.

The term "Second Agents" hereinafter refers collectively to pharmaceutical compounds or agents that are sorbitol dehydrogenase inhibitors, selective serotonin reuptake inhibitors, 3-hydroxy-3-methylglutaryl coenzyme A reductase inhibitors, angiotensin converting enzyme inhibitors, glycogen phosphorylase inhibitors, angiotensin II receptor antagonists, γ-aminobutyric acid agonist, phosphodiesterase type 5 inhibitors, a prodrug of said compounds or agents, or a pharmaceutically acceptable salt of such compound, agent or prodrug. Use of the term in singular form, as in "a Second Agent" hereinafter refers to a pharmaceutical agent selected from said Second Agents. A Second Agent may be a pharmaceutical agent that shares more than one of the foregoing characteristics.

An additional aspect of this invention relates to pharmaceutical compositions comprising a compound of formula I of this invention, and a Second Agent. Such compositions are hereinafter referred to collectively as the "combination compositions".

This invention also relates to therapeutic methods for treating or preventing diabetic complications in a mammal wherein a compound of formula I of this invention and a Second Agent are administered together as part of the same pharmaceutical composition or separately. Such methods are hereinafter referred to collectively as the "combination therapies" of this invention. Combination therapies include therapeutic methods wherein a compound of formula I of this invention and a Second Agent are administered together as part of the same pharmaceutical composition and to methods wherein these two agents are administered separately, either simultaneously or sequentially in any order.

This invention further provides pharmaceutical kits comprising a compound of formula I of this invention and a Second Agent. Such kits may hereinafter be referred to as the "kits" of this invention.

Any selective serotonin reuptake inhibitor (SSRI) may be used as the Second Agent in the combination compositions, combination therapies and kits of this invention. The term selective serotonin reuptake inhibitor refers to an agent which inhibits the reuptake of serotonin by afferent neurons. Such inhibition is readily determined by those skilled in the art according to standard assays such as those disclosed in U.S. Pat. No. 4,536,518 and other U.S. patents recited in the next paragraph.

Preferred selective serotonin reuptake inhibitors which may be used in accordance with this invention include femoxetine, which may be prepared as described in U.S. Pat. No. 3,912,743; fluoxetine, which may be prepared as described in U.S. Pat. No. 4,314,081; fluvoxamine, which may be prepared as described in U.S. Pat. No. 4,085,225; indalpine, which may be prepared as described in U.S. Pat. No. 4,064,255; indeloxazine, which may be prepared as described in U.S. Pat. No. 4,109,088; milnacipran, which may be prepared as described in U.S. Pat. No. 4,478,836; paroxetine, which may be prepared as described in U.S. Pat. No. 3,912,743 or U.S. Pat. No. 4,007,196; sertraline, which may be prepared as described in U.S. Pat. No. 4,536,518; sibutramine, which may be prepared as described in U.S. Pat. No. 4,929,629; and zimeldine, which may be prepared as described in U.S. Pat. No. 3,928,369. Fluoxetine is also known as Prozac®. Sertraline hydrochloride is also known as Zoloft®. Sibutramine is also known as Meridia®. The disclosures thereof are incorporated herein by reference.

Selective serotonin reuptake inhibitors are preferably administered in amounts ranging from about 0.01 mg/kg/day to about 500 mg/kg/day in single or divided doses, preferably about 10 mg to about 300 mg per day for an average subject, depending upon the selective serotonin reuptake inhibitor and the route of administration. However, some variation in dosage will necessarily occur depending on the condition of the subject being treated. The individual responsible for dosing will, in any event, determine the appropriate dose for the individual subject.

Any 3-hydroxy-3-methylglutaryl coenzyme A (HMG-CoA) reductase inhibitor may be used as the Second Agent in the combination compositions, combination therapies and kits of this invention. The term 3-hydroxy-3-methylglutaryl coenzyme A (HMG-CoA) reductase inhibitor refers to a pharmaceutical agent which inhibits the enzyme 3-hydroxy-3-methylglutaryl-coenzyme A (HMG-CoA) reductase. This enzyme is involved in the conversion of HMG-CoA to mevalonate, which is one of the steps in cholesterol biosynthesis. Such inhibition is readily determined according to standard assays well known to those skilled in the art.

Preferred 3-hydroxy-3-methylglutaryl coenzyme A reductase inhibitors which may be used in accordance with this invention include atorvastatin, disclosed in U.S. Pat. No. 4,681,893, atorvastatin calcium, disclosed in U.S. Pat. No. 5,273,995, cerivastatin, disclosed in U.S. Pat. No. 5,502,199, dalvastatin, disclosed in European Patent Application Publication No. 738,510 A2, fluindostatin, disclosed in European Patent Application Publication No. 363,934 A1, fluvastatin, disclosed in U.S. Pat. No. 4,739,073, lovastatin, disclosed in U.S. Pat. No. 4,231,938, mevastatin, disclosed in U.S. Pat. No. 3,983,140, pravastatin, disclosed in U.S. Pat. No. 4,346,227, simvastatin, disclosed in U.S. Pat. No. 4,444,784 and velostatin, disclosed in U.S. Pat. No. 4,448,784 and U.S. Pat. No. 4,450,171, all of which are incorporated herein by reference. Especially preferred 3-hydroxy-3-methylglutaryl coenzyme A reductase inhibitors include atorvastatin, atorvastatin calcium, also known as Liptor®, lovastatin, also known as Mevacor®, pravastatin, also known as Pravachol®, and simvastatin, also known as Zocor®.

3-Hydroxy-3-methylglutaryl coenzyme A reductase inhibitors are preferably administered in amounts ranging from about 0.1 mg/kg to about 1000 mg/kg/day in single or divided doses, preferably about 1 mg/kg/day to about 200 mg/kg/day for an average subject, depending upon the 3-hydroxy-3-methylglutaryl coenzyme A reductase inhibitor and the route of administration. However, some variation in dosage will necessarily occur depending on the condition of the subject being treated. The individual responsible for dosing will, in any event, determine the appropriate dose for the individual subject.

Any angiotensin converting enzyme (ACE) inhibitor may be used as the Second Agent in the combination compositions, combination therapies and kits of this invention. The term angiotensin converting enzyme inhibitor refers to a pharmaceutical agent which inhibits angiotensin converting enzyme activity. Angiotensin converting enzyme is involved in the conversion of angiotensin I to the vasoconstrictor, angiotensin II. The activity of angiotensin converting enzyme inhibitors may readily be determined by methods known to those skilled in the art, including any of the standard assays described in the patents listed below.

Preferred angiotensin converting enzyme inhibitors include: alacepril, disclosed in U.S. Pat. No. 4,248,883; benazepril, disclosed in U.S. Pat. No. 4,410,520; captopril, disclosed in U.S. Pat. Nos. 4,046,889 and 4,105,776; ceronapril, disclosed in U.S. Pat. No. 4,452,790; delapril, disclosed in U.S. Pat. No. 4,385,051; enalapril, disclosed in U.S. Pat. No. 4,374,829; fosinopril, disclosed in U.S. Pat. No. 4,337,201; imadapril, disclosed in U.S. Pat. No. 4,508,727; lisinopril, disclosed in U.S. Pat. No. 4,555,502; moexipril, disclosed in U.S. Pat. No. 4,344,949; moveltopril, disclosed in Belgian Patent No. 893,553; perindopril, disclosed in U.S. Pat. No. 4,508,729; quinapril, disclosed in U.S. Pat. No. 4,344,949; ramipril, disclosed in U.S. Pat. No. 4,587,258; spirapril, disclosed in U.S. Pat. No. 4,470,972; temocapril, disclosed in U.S. Pat. No. 4,699,905; and trandolapril, disclosed in U.S. Pat. No. 4,933,361. The disclosures of all such patents are incorporated herein by reference.

Angiotensin converting enzyme inhibitors are preferably administered in amounts ranging from about 0.01 mg/kg/day to about 500 mg/kg/day in single or divided doses, preferably about 10 mg to about 300 mg per day for an average subject, depending upon the angiotensin converting enzyme inhibitor and the route of administration. However, some variation in dosage will necessarily occur depending on the condition of the subject being treated. The individual responsible for dosing will, in any event, determine the appropriate dose for the individual subject.

Any angiotensin-II receptor (A-II), antagonist may be used as the Second Agent in the combination compositions, combination therapies and kits of this invention. The term angiotensin-II receptor antagonist refers to a pharmaceutical agent that blocks the vasoconstrictor effects of angiotensin II by blocking the binding of angiotensin II to the $AT_1$ receptor found in many tissues, (e.g., vascular smooth muscle, adrenal gland). The activity of angiotensin-II receptor antagonist may readily be determined by methods known to those skilled in the art, including any of the standard assays described in the patents listed below.

Preferred angiotensin-II receptor antagonists include: candesartan, which may be prepared as disclosed in U.S. Pat. No. 5,196,444; eprosartan, which may be prepared as disclosed in U.S. Pat. No. 5,185,351; irbesartan, which may be prepared as disclosed in U.S. Pat. No. 5,270,317; losartan, which may be prepared as disclosed in U.S. Pat. No. 5,138,069; and valsartan, which may be prepared as disclosed in U.S. Pat. No. 5,399,578. The disclosures thereof are incorporated herein by reference. More preferred angiotensin-II receptor antagonists are losartan, irbesartan and valsartan.

Angiotensin-II receptor antagonists are preferably administered in amounts ranging from about 0.01 mg/kg/day to about 500 mg/kg/day in single or divided doses, preferably about 10 mg to about 300 mg per day for an average subject, depending upon the angiotensin-II receptor antagonist and the route of administration. However, some variation in dosage will necessarily occur depending on the condition of the subject being treated. The individual responsible for dosing will, in any event, determine the appropriate dose for the individual subject.

Any γ-aminobutyric acid (GABA) agonist may be used as the Second Agent in the combination compositions, combination therapies and kits of this invention. The term γ-aminobutyric acid agonist refers to a pharmaceutical agent that binds to GABA receptors in the mammalian central nervous system. GABA is the major inhibitory neurotransmitter in the mammalian central nervous system. The activity of γ-aminobutyric acid (GABA) agonist may readily be determined by methods known to those skilled in the art, including the procedures disclosed in Janssens de Verebeke, P. et al., Biochem. Pharmacol., 31, 2257–2261 (1982), Loscher, W., Biochem. Pharmacol., 31, 837–842, (1982) and/or Phillips, N. et al., Biochem. Pharmacol., 31, 2257–2261.

Preferred γ-aminobutyric acid agonist include: muscimol, progabide, riluzole, baclofen, gabapentin (Neurontin®), vigabatrin, valproic acid, tiagabine (Gabitril®), lamotrigine (Lamictal®), pregabalin, phenytoin (Dilantin®), carbamazepine (Tegretol®), topiramate (Topamax®) and analogs, derivatives, prodrugs and pharmaceutically acceptable salts of those γ-aminobutyric acid agonist agonists.

In general, in accordance with this invention, the γ-aminobutyric acid agonist used in the combinations, pharmaceutical compositions, methods and kits of this invention will be administered in a dosage amount of about 4 mg/kg body weight of the subject to be treated per day to about 60 mg/kg body weight of the subject to be treated per day, in single or divided doses. However, some variation in dosage will necessarily occur depending upon the condition of the subject being treated. The person responsible for administration will, in any event, determine the appropriate dose for the individual subject. In particular, when used as they-aminobutyric acid agonist agonist in this invention, pregabalin will be dosed at about 300 mg to about 1200 mg per day; gabapentin will be dosed at about 600 mg to about 3600 mg per day.

Any glycogen phosphorylase inhibitor (GPI) may be used as the Second Agent in the combination compositions, combination therapies and kits of this invention. The term glycogen phosphorylase inhibitor refers to any substance or agent or any combination of substances and/or agents which reduces, retards, or eliminates the enzymatic action of glycogen phosphorylase. Such actions are readily determined by those skilled in the art according to standard assays as described in U.S. Pat. No. 5,988,463.

U.S. Pat. No. 5,988,463, PCT application publication WO 96/39384 and PCT application publication WO96/39385 exemplify glycogen phosphorylase inhibitors which can be used in the combination compositions, methods and kits of this invention, and refer to methods of preparing those glycogen phosphorylase inhibitors.

Glycogen phosphorylase inhibitors are preferably administered in amounts ranging from about 0.005 mg/kg/day to about 50 mg/kg/day in single or divided doses, preferably about 0.1 mg/kg to about 15 mg/kg per day for an average subject, depending upon the glycogen phosphorylase inhibitor and the route of administration. However, some variation in dosage will necessarily occur depending on the condition of the subject being treated. The individual responsible for dosing will, in any event, determine the appropriate dose for the individual subject.

Any sorbitol dehydrogenase inhibitor (SDI) may be used as the Second Agent in the combination compositions, combination therapies and kits of this invention. The term sorbitol dehydrogenase inhibitor refers to any substance or agent or any combination of substances and/or agents which reduces, retards, or eliminates the enzymatic action of sorbitol dehydrogenase. Sorbitol dehydrogenase is believed to catalyze the oxidation of sorbitol to fructose.

Sorbitol dehydrogenase inhibitors are disclosed in commonly assigned U.S. Pat. No. 5,728,704, U.S. Pat. No. 5,866,578 and PCT application publication WO 00/59510, incorporated herein by reference.

The activity of sorbitol dehydrogenase inhibitors may be evaluated using the assays and methods disclosed in commonly assigned PCT application publication WO 00/59510 and other assays and methods known by those skilled in the art.

Sorbitol dehydrogenase inhibitors are preferably administered in amounts ranging from about 0.001 mg/kg/day to about 100 mg/kg/day in single or divided doses, preferably about 0.01 mg/kg to about 10 mg/kg per day for an average subject, depending upon the sorbitol dehydrogenase inhibitor and the route of administration. However, some variation in dosage will necessarily occur depending on the condition of the subject being treated. The person responsible for administration will, in any event, determine the appropriate dose for the individual subject.

Any phosphodiesterase type 5 (PDE-5) inhibitor may be used as the Second Agent in the combination compositions, combination therapies and kits of this invention. The term phosphodiesterase type 5 inhibitor refers to any substance or agent or any combination of substances and/or agents which reduces, retards, or eliminates the enzymatic action of cyclic guanosine monophosphate (cGMP)-specific phosphodiesterase type 5. Such actions are readily determined by those skilled in the art according to assays as described in PCT application publication WO 00/24745.

The following patent publications exemplify phosphodiesterase type 5 inhibitors which can be used in the combination compositions, methods and kits of this invention, and refer to methods of preparing those phosphodiesterase type 5 (PDE-5) inhibitors: PCT application publication WO 00/24745; PCT application publication WO 94/28902; European Patent application publication 0463756A1; European Patent application publication 0526004A1 and European Patent application publication 0201188A2. A preferred phosphodiesterase type 5 inhibitor is sildenafil citrate, also known as Viagra®.

Phosphodiesterase type 5 inhibitors are preferably administered in amounts ranging from about 5 mg/day to about 500 mg/day in single or divided doses, preferably about 10 mg/day to about 250 mg/day, for an average subject depending upon the phosphodiesterase type 5 inhibitor and the route of administration. However, some variation in dosage will necessarily occur depending on the condition of the subject being treated. The individual responsible for dosing will, in any event, determine the appropriate dose for the individual subject.

In the aspects of this invention related to therapeutic methods of treating or preventing diabetic complications wherein a compound of formula I of this invention and a Second Agent are administered together as part of the same pharmaceutical composition and to methods wherein these two agents are administered separately, the appropriate dosage regimen, the amount of each dose administered and the intervals between doses of the active agents will again depend upon the compound of formula I of this invention and the Second Agent being used, the type of pharmaceutical compositions being used, the characteristics of the subject being treated and the severity of the conditions.

Administration of the compounds and pharmaceutical compositions of this invention may be performed via any method which delivers a compound or composition of this invention preferentially to the desired tissue (e.g., nerve, kidney, lens, retina and/or cardiac tissues). These methods include oral routes, parenteral, intraduodenal routes, etc, and may be administered in single (e.g., once daily) or multiple doses or via constant infusion.

The pharmaceutical compositions of this invention may be administered to a subject in need of treatment by a variety of conventional routes of administration, including orally, topically, parenterally, e.g., intravenously, subcutaneously or intramedullary. Further, the pharmaceutical compositions of this invention may be administered intranasally, as a suppository or using a "flash" formulation, i.e., allowing the medication to dissolve in the mouth without the need to use water.

The compounds of this invention may be administered alone or in combination with pharmaceutically acceptable carriers, vehicles or diluents, in either single or multiple doses. Suitable pharmaceutical carriers, vehicles and diluents include inert solid diluents or fillers, sterile aqueous solutions and various organic solvents. The pharmaceutical compositions formed by combining the compounds of this invention and the pharmaceutically acceptable carriers, vehicles or diluents are then readily administered in a variety of dosage forms such as tablets, powders, lozenges, syrups, injectable solutions and the like. These pharmaceutical compositions can, if desired, contain additional ingredients such as flavorings, binders, excipients and the like. Thus, for purposes of oral administration, tablets containing various excipients such as sodium citrate, calcium carbonate and/or calcium phosphate may be employed along with various disintegrants such as starch, alginic acid and/or certain complex silicates, together with binding agents such as polyvinylpyrrolidone, sucrose, gelatin and/or acacia. Additionally, lubricating agents such as magnesium stearate, sodium laurylsulfate and talc are often useful for tabletting purposes. Solid compositions of a similar type may also be employed as fillers in soft and hard filled gelatin capsules. Preferred materials for this include lactose or milk sugar and high molecular weight polyethylene glycols. When aqueous suspensions or elixirs are desired for oral administration, the active pharmaceutical agent therein may be combined with various sweetening or flavoring agents, coloring matter or dyes and, if desired, emulsifying or suspending agents, together with diluents such as water, ethanol, propylene glycol, glycerin and/or combinations thereof.

For parenteral administration, solutions of the compounds of this invention in sesame or peanut oil, aqueous propylene glycol, or in sterile aqueous solutions may be employed. Such aqueous solutions should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, the sterile aqueous media employed are all readily available by standard techniques known to those skilled in the art.

Generally, a composition of this invention is administered orally, or parenterally (e.g., intravenous, intramuscular, subcutaneous or intramedullary). Topical administration may also be indicated, for example, where the patient is suffering from gastrointestinal disorders or whenever the medication is best applied to the surface of a tissue or organ as determined by the attending physician.

Buccal administration of a composition of this invention may take the form of tablets or lozenges formulated in a conventional manner.

For intranasal administration or administration by inhalation, the compounds of the invention are conveniently delivered in the form of a solution or suspension from a pump spray container that is squeezed or pumped by the patient or as an aerosol spray presentation from a pressurized container or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of a compound of this invention. Capsules and cartridges (made, for example, from gelatin) for use in an inhaler or insufflator may be formulated containing a powder mix of a compound or compounds of the invention and a suitable powder base such as lactose or starch.

For purposes of transdermal (e.g., topical) administration, dilute sterile, aqueous or partially aqueous solutions (usually in about 0.1% to 5% concentration), otherwise similar to the above parenteral solutions, are prepared.

Methods of preparing various pharmaceutical compositions with a certain amount of active ingredient are known, or will be apparent in light of this disclosure, to those skilled in this art. For examples of methods of preparing pharmaceutical compositions, see *Remington's Pharmaceutical Sciences*, Mack Publishing Company, Easton, Pa., 19th Edition (1995).

In the aspects of this invention related to the combination compositions, wherein the compositions contain an amount of both a compound of formula I of this invention, a prodrug thereof or a pharmaceutically acceptable salt of said compound or prodrug and a Second Agent, the amount of each such ingredient may independently be, 0.0001%–95% of the total amount of the composition, provided, of course, that the total amount does not exceed 100%. In any event, the composition or formulation to be administered will contain a quantity of each of the components of the composition according to the invention in an amount effective to treat the disease/condition of the subject being treated.

Since the present invention has an aspect that relates to the treatment of the disease/conditions described herein with a combination of active ingredients which may be administered separately, the invention also relates to combining separate pharmaceutical compositions in kit form. The kit comprises two separate pharmaceutical compositions: a first pharmaceutical composition comprising a compound of formula I of this invention, a prodrug thereof or a pharmaceutically acceptable salt of such compound or prodrug; and a second pharmaceutical composition comprising a agent selected from a sorbitol dehydrogenase inhibitor, a selective serotonin reuptake inhibitor, a 3-hydroxy-3-methylglutaryl coenzyme A reductase inhibitor, an angiotensin converting enzyme inhibitor, a glycogen phosphorylase inhibitor, a angiotensin II receptor antagonist, a γ-aminobutyric acid agonist or a phosphodiesterase type 5 inhibitor, a prodrug thereof or a pharmaceutically acceptable salt of said second agent or prodrug as described above. The kit comprises a container for containing the separate compositions such as a divided bottle or a divided foil packet. Typically the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

An example of such a kit is a so-called blister pack. Blister packs are well known in the packaging industry and are widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a memory aid on the kit, e.g., in the form of numbers next to the tablets or capsules whereby the numbers correspond with the days of the regimen which the tablets or capsules so specified should be ingested. Another example of such a memory aid is a calendar printed on the card, e.g., as follows "First Week, Monday, Tuesday, . . . etc . . . . Second Week, Monday, Tuesday, . . . " etc. Other variations of memory aids will be readily apparent. A "daily dose" can be a single tablet or capsule or several tablets or capsules to be taken on a given day. Also, a daily dose of a compound of this invention can consist of one tablet or capsule while a daily dose of the Second Agent can consist of several tablets or capsules, or vice versa. The memory aid should reflect this.

In another specific embodiment of the invention, a dispenser designed to dispense the daily doses one at a time in the order of their intended use is provided. Preferably, the dispenser is equipped with a memory-aid, so as to further facilitate compliance with the regimen. An example of such a memory-aid is a mechanical counter which indicates the number of daily doses that has been dispensed. Another example of such a memory-aid is a battery-powered microchip memory coupled with a liquid crystal readout, or audible reminder signal which, for example, reads out the date that the last daily dose has been taken and/or reminds one when the next dose is to be taken.

The journal articles and scientific references, patents and patent application publications cited above are wholly incorporated herein by reference.

GENERAL EXPERIMENTAL PROCEDURES

Melting points were determined on a Thomas-Hoover capillary melting point apparatus, and are uncorrected. $^1$H NMR spectra were obtained on a Bruker AM-250 (Bruker Co., Billerica, Mass.), a Bruker AM-300, a Varian XL-300 (Varian Co., Palo Alto, Calif.), or a Varian Unity 400 at about 23° C. at 250, 300, or 400 MHz for proton. Chemical shifts are reported in parts per million (6) relative to residual chloroform (7.26 ppm), dimethylsulfoxide (2.49 ppm), or methanol (3.30 ppm) as an internal reference. The peak shapes and descriptors for the peak shapes are denoted as follows: s, singlet; d, doublet; t, triplet; q, quartet; m, multiplet; c, complex; br, broad; app, apparent. Low-resolution mass spectra were obtained under thermospray (TS) conditions on a Fisons (now Micromass) Trio 1000 Mass Spectrometer (Micromass Inc., Beverly, Mass.), under chemical-ionization (Cl) conditions on a Hewlett Packard 5989A Particle Beam Mass Spectrometer (Hewlett Packard Co., Palo Alto, Calif.), or under atmospheric pressure chemical ionization (APCI) on a Fisons (now Micromass) Platform II Spectrometer.

EXAMPLE 1

6-(3-Trifluoromethyl-benzenesulfonyl)-2H-pyridazin-3-one

A mixture of 3,6-dichloropyridazine (4.44 g), 3-trifluoromethylphenyl sulfinic acid sodium salt (6.93 g), isopropanol (30 mL), and water (1 mL) was prepared and refluxed for 18 hours. The reaction mixture was then cooled, diluted with water (100 mL) and the precipitated solid was collected. The solid was triturated with n-propanol and the solid was collected to obtain the title compound (25%, 2.3 g).

EXAMPLE 2

6-(2-Fluoro-benzenesulfonyl)-2H-pyridazin-3-one

Step 1: 3-(2-Fluoro-phenylsulfanyl)-6-methoxy-pyridazine.

To a clear solution of 4-fluorothiophenol (2.56 g) in DMF (10 mL) was added 3-chloro-6-methoxy-pyridazine (3.18 g) and stirred at room temperature for 1 hour. The reaction mixture was quenched with water (30 mL) and extracted with ethyl acetate (50 mL). The ethyl acetate layer was collected, washed with water (2×20 mL) and the organic portion was collected, dried over anhydrous sodium sulfate, filtered and the filtrate was evaporated to obtain crude 3-(2-fluoro-phenylsulfanyl)-6-methoxy-pyridazine (85%, 4.0 g, mp, 58–62° C.; mass spectrum M$^+$, 236).

Step 2: 3-(2-Fluoro-benzenesulfonyl)-6-methoxy-pyridazine.

A mixture of 3-(2-fluoro-phenylsulfanyl)-6-methoxy-pyridazine (500 mg), m-chloroperbenzoic acid (MCPBA) (1.04 g) and methylene dichloride (10 mL) was prepared and stirred at room temperature for two hours. The reaction mixture was diluted with methylene dichloride and the methylene dichloride layer was washed with saturated sodium bicarbonate (10 mL) and then with water (2×20 mL). The methylene dichloride layer was collected, dried over anhydrous sodium sulfate, filtered and the filtrate was evaporated to dryness. The residue was purified by silica gel chromatography (3:1 ethyl acetate/hexane as eluent) to obtain 3-(2-fluoro-benzenesulfonyl)-6-methoxy-pyridazine as a white solid (51%, 290 mg; NMR, 4.19 (s, 3H), 7.13 (d, 1H), 7.21 (d, 1H), 8.13 (m, 4H).

Step 3: 6-(2-Fluoro-benzenesulfonyl)-2H-pyridazin-3-one.

A mixture of 3-(2-fluoro-benzenesulfonyl)-6-methoxy-pyridazine (200 mg) and concentrated hydrochloric acid (2 mL) was prepared and refluxed for one hour. The reaction mixture was cooled and diluted with water (20 mL). Sufficient 40% aqueous sodium hydroxide was then added to adjust the pH of the mixture to 3 and the mixture was extracted with ethyl acetate (2×20 mL). The ethyl acetate extract portions were collected and combined, dried over anhydrous sodium sulfate and filtered. The filtrate was evaporated to obtain the title compound as a white solid (45%, 80 mg), mp, 173–176° C.; NMR, 7.06 (d, 1H), 7.23 (m, 1H), 7.3 (m, 1H), 7.89 (d, 1H), 8.02 (m, 2H) and 11.66 (s, 1H).

EXAMPLE 3

6-(4-Bromo-2-fluoro-benzenesulfonyl)-2H-pyridazin-3-one

Step 1: 3-(4-Bromo-2-fluoro-phenylsulfanyl)-6-methoxy-pyridazine.

A mixture of 2-fluoro-4-bromothiophenol (300 mg), 2,6-dichloro-pyridazine (149 mg), potassium carbonate (400 mg) and acetone (6 mL) was prepared and refluxed for two hours. The acetone from the mixture was evaporated and the resulting residue was dissolved in a solution of methanol (3 mL) and sodium metal (166 mg). The resulting solution was refluxed for 1 hour. Evaporation of methanol afforded 3-(4-bromo-2-fluoro-phenylsulfanyl)-6-methoxy-pyridazine, which was not isolated but was immediately used in Step 2.

Step 2: 3-(4-Bromo-2-fluoro-benzenesulfonyl)-6-methoxy-pyridazine.

The product of Step 1 (400 mg) was dissolved in chloroform(10 mL) and m-chloroperbenzoic acid (MCPBA) (770 mg) was added to the resulting solution. The reaction mixture was stirred overnight at room temperature. The solvent was evaporated and the resulting residue was purified by silica gel chromatography (90% hexane/10% ethyl acetate as eluent) to obtain the title compound (264 mg, 60%): mass spectrum, $M^+$, 346.

Step 3: 6-(4-Bromo-2-fluoro-benzenesulfonyl)-2H-pyridazin-3-one.

A mixture of 3-(4-bromo-2-fluoro-benzenesulfonyl)-6-methoxy-pyridazine (260 mg), dioxane (5 mL), and concentrated hydrochloric acid (1 mL) was prepared and refluxed for two hours. The reaction mixture was then evaporated to dryness. The resulting residue was triturated with water and the precipitated solid was collected and air-dried to obtain the title compound (90%, 225 mg); mp, >220° C.; NMR 7.05 (d, 1H), 7.7 (d, 1H), 7.9 (m, 3H), 13.8 (s, 1H).

acidified to pH 3 with concentrated hydrochloric acid and then extracted with ethyl acetate (3×10 mL). The ethyl acetate extract was evaporated and the residue was purified by silica gel chromatography to afford 343-chloro-phenylsulfanyl)-6-methoxy-pyridazine ($M^+$, 253).

Step 2: 3-(3-Chloro-benzenesulfonyl)-6-methoxy-pyridazine.

A mixture of 3-(3-chloro-phenylsulfanyl)-6-methoxy-pyridazine (529 mg), m-chloroperbenzoic acid (MCPBA) (760 mg) and chloroform (20 mL) was prepared and stirred at room temperature for two hours. The reaction mixture was diluted with 5% sodium thiosulfate (20 mL) followed by water (30 mL). The chloroform layer was collected, dried over anhydrous sodium sulfate, filtered and the dried chloroform portion was evaporated to dryness. The resulting solid residue was purified by silica gel chromatography (3:1 hexane/ethyl acetate as eluent) to obtain 3-(3-chloro-benzenesulfonyl)-6-methoxy-pyridazine (29%, 173 mg); mass spectrum, $M^+$, 285.

Step 3: 6-(3-Chloro-benzenesulfonyl)-2H-pyridazin-3-one

A mixture of 3-(3-chloro-benzenesulfonyl)-6-methoxy-pyridazine (148 mg), dioxane (2 mL) and concentrated hydrochloric acid (0.5 mL) was prepared and refluxed for 30 minutes. The reaction mixture was then evaporated to dryness and the residue was extracted with ethyl acetate (2×10 mL). The ethyl acetate mixture was collected, dried over anhydrous sodium sulfate, filtered and the filtrate was evaporated to dryness to afford 6-(3-chloro-benzenesulfonyl)-2H-pyridazin-3-one as white solid (38%, 61 mg); mp, 222–223° C.: NMR, 7.11 (d, 1H), 7.74 (t, 1H), 7.86–8.04 (m, 4H), 13.86 (s, 1H).

Examples 4A to 4N were prepared from the appropriate starting materials in a manner analogous to the method of Example 4.

| Example | Compound | MP ° C. |
|---|---|---|
| 4A | 6-(4-Fluoro-benzenesulfonyl)-2H-pyridazin-3-one | >225 |
| 4B | 6-(4-Trifluoromethyl-benzenesulfonyl)-2H-pyridazin-3-one | >220 |
| 4C | 6-(2-Bromo-benzenesulfonyl)-2H-pyridazin-3-one | 210–213 |
| 4D | 6-(3,4-Dichloro-benzenesulfonyl)-2H-pyridazin-3-one | 166–168 |
| 4E | 6-(4-Methoxy-benzenesulfonyl)-2H-pyridazin-3-one | 111–113 |
| 4F | 6-(2-Chloro-4-fluoro-benzenesulfonyl)-2H-pyridazin-3-one | 205–208 |
| 4G | 6-(4-Chloro-benzenesulfonyl)-2H-pyridazin-3-one | >220 |
| 4H | 6-(2-Chloro-benzenesulfonyl)-2H-pyridazin-3-one | 220-222 |
| 4I | 6-(3-Bromo-benzenesulfonyl)-2H-pyridazin-3-one | >220 |
| 4K | 6-(4-Bromo-2-fluoro-phenylmethanesulfonyl)-2H-pyridazin-3-one | >220 |
| 4L | 6-(2,6-Dichloro-phenylmethanesulfonyl)-2H-pyridazin-3-one | 219–220 |
| 4M | 6-(3-Chloro-5-methyl-benzenesulfonyl)-2H-pyridazin-3-one | >250 |
| 4N | 6-(2-Chloro-4,6-difluoro-benzenesulfonyl)-2H-pyridazin-3-one | >250 |

EXAMPLE 4

6-(3-Chloro-benzenesulfonyl)-2H-pyridazin-3-one

Step 1: 3-(3-Chloro-phenylsulfanyl)-6-methoxy-pyridazine.

Sodium metal (218 mg) was dissolved in methanol (10 mL). 3 Chlorothiophenol was added and stirred for one hour at room temperature. The excess methanol was evaporated and to the dry residue was added toluene (20 mL) and 3-chloro-6-methoxypyridazine (1.1 g). The reaction mixture was refluxed for four hours, cooled to room temperature and then poured into water (30 mL). The pH of the solution was first adjusted to 10 with 20% potassium hydroxide and extracted with ethyl acetate (2×20 mL). The aqueous layer from the extraction was collected. The aqueous portion was

EXAMPLE 5

6-(2,4-Dichloro-benzenesulfonyl)-2H-pyridazin-3-one

Step 1: 6-(2,4-Dichloro-phenylsulfanyl)-2H-pyridazin-3-one.

Potassium t-butoxide (1.1 g) was added to a solution of 2,4-dichlorothiophenol (1.8 g) in N,N-dimethylformamide (DM F) (5 mL). The mixture was stirred at room temperature for 10 minutes and then 6-chloro 2H-pyridazin-3-one (1.31 g) was added. The reaction mixture was stirred at 100° C. for five hours. The mixture was then cooled to room temperature, poured into water (20 mL) and 20% potassium hydroxide (5 mL) was added. The resulting dark solution was extracted with ethyl acetate (2×10 mL). The aqueous layer was collected and the pH was adjusted to 3 with concentrated hydrochloric acid. The solution was then extracted with ethyl acetate (3×10 mL). The ethyl acetate layer was collected, dried over anhydrous sodium sulfate, filtered and evaporated to obtain a crude product, which was purified by silica gel chromatography (1:1 ethyl acetate/hexane as eluent) to afford 6-(2,4-dichloro-phenylsulfanyl)-2H-pyridazin-3-one (418 mg, 15%); NMR 6.88 (d, 1H), 7.10 (d, 1H), 7.24 (dd, 1H), 7.48 (d, 11H), 7.52 (d, 1H).

Step 2: 6-(2,4-Dichloro-benzenesulfonyl)-2H-pyridazin-3-one.

A mixture of 6-(2,4-dichloro-phenylsulfanyl)-2H-pyridazin-3-one (418 mg), peracetic acid (3.2 mL) and acetic acid (3.2 mL) was prepared and stirred for 2.5 hours at 80° C. The reaction mixture was then cooled to room temperature and poured into water (50 mL). The resulting white solid was collected and dried to obtain the title product, 6-(2,4-dichloro-benzenesulfonyl)-2H-pyridazin-3-one, (37%, 173 mg); mp, 202–203° C.; NMR 7.15 (d, 1H), 7.81 (dd, 1H), 8.03 (m, 2H), 8.25 (d, 1H), 13.88 (s, 1H).

Examples 5A to 5I were prepared from the appropriate starting materials in a manner analogous to the method of Example 5.

| Example | Compound | MP ° C. |
|---|---|---|
| 5A | 6-(2-Chloro-benzenesulfonyl)-2H-pyridazin-3-one | 220–222 |
| 5B | 6-(2,4-Difluoro-benzenesulfonyl)-2H-pyridazin-3-one | 186–188 |
| 5C | 6-(Naphthalene-1-sulfonyl)-2H-pyridazin-3-one | 225–226 |
| 5D | 6-(2,4-Dichloro-benzenesulfonyl)-2H-pyridazin-3-one | 202–203 |
| 5E | 6-(2-Fluoro-benzenesulfonyl)-2H-pyridazin-3-one | 189–191 |
| 5F | 6-(2,3-Dichloro-benzenesulfonyl)-2H-pyridazin-3-one | 224–225 |
| 5G | 6-(2,5-Dichloro-benzenesulfonyl)-2H-pyridazin-3-one | 229–232 |
| 5H | 6-(2,6-Dichloro-benzenesulfonyl)-2H-pyridazin-3-one | 118–120 |
| 5I | 6-(2,3-Difluoro-benzenesulfonyl)-2H-pyridazin-3-one | >225 |

EXAMPLE 6

6-(2-Hydroxy-benzenesulfonyl)-2H-pyridazin-3-one

A mixture of 6-(2-methoxy-benzenesulfonyl)-2H-pyridazin-3-one (100 mg) and aluminum tri-bromide (2 g) was prepared and heated at 100° C. for two hours. The reaction mixture was cooled and water (10 mL) was added. The mixture was then extracted with chloroform. The organic extract was washed with water (2×10 mL), dried over anhydrous sodium sulfate and evaporated. The resulting residue was triturated with isopropyl ether and the resulting solid was collected by filtration to afford the title compound (61%, 58 mg), $^1$HNMR (CDCl$_3$, 300 MHz), δ 7.0 (m, 3H), 7.6 (m, 2H), 7.8 (d, 1H).

EXAMPLE 7

3-(2-Chloro-benzenesulfonyl)-6-methoxy-pyridazine, N-oxide

A mixture of 3-(2-chloro-phenylsulfanyl)-6-methoxy-pyridazine, m-chloroperbenzoic acid (MCPBA) (4.0 g), and chloroform (30 mL) was prepared and refluxed for 30 hours. Mass spectrum analysis of an aliquot of the reaction sample showed complete conversion to the desired sulfone-N-oxide (M+, 301). The reaction was cooled, washed successively with sodium sulfite (10% solution, 20 mL), sodium carbonate (10% solution, 20 mL), and water (2×20 mL). The chloroform layer was collected, dried over anhydrous sodium sulfate, filtered and the filtrate was evaporated to obtain a crude solid. The crude solid was purified by silica gel chromatography (1:1 ethyl acetate/hexane as eluent) to afford the title compound (38%, 425 mg); mp, 148–153° C.; (38%, 425 mg); NMR 4.01 (s, 3H), 6.80 (d, 1H), 7.42 (m, 1H), 7.57 (m, 2H), 8.38 (d, 1H), 8.46 (m, 1H).

EXAMPLE 8

3-(2-Chloro-4-fluoro-benzenesulfonyl)-6-methoxy-pyridazine, N-oxide

The title compound was prepared according to a procedure analgous to that of Example 7 using 3-(2-chloro-4-fluoro-phenylsulfanyl)-6-methoxy-pyridazine as the starting compound. (60%); mp, 159–161° C.; NMR δ 4.01 (s, 3H), 6.80 (d, 1H), 7.15 (dd, 1H), 7.25 (dd, 1H), 8.37 (d, 1H), 8.49 (m, 1H).

EXAMPLE 9

3-(2-Chloro-benzenesulfonyl)-6-methoxy-pyridazine

A mixture of 3-(2-chloro-benzenesulfonyl)-6-methoxy-pyridazine, N-oxide, N-oxide from Example 7 (317 mg) and triethyphosphite (3 mL) was heated to 100° C. for four hours. The reaction mixture was cooled to room temperature, poured into water (20 mL), and extracted with ethyl acetate (2×10 mL). The organic extract was evaporated to dryness and the crude product was purified by silica gel chromatography (1:1 ethyl acetate/hexane as eluent). (48%, 143 mg); NMR δ 4.19 (s, 3H), 7.19 (d, 1H), 7.43 (dd, 2H), 7.58 (m, 2H), 8.27 (d, 1H), 8.44 (dd, 2H).

EXAMPLE 10

3-(2-Chloro-4-fluoro-benzenesulfonyl)-6-methoxy-pyridazine

The title compound was prepared according to procedure of Example 9 starting from 3-(2-chloro-4-fluoro-benzenesulfonyl)-6-methoxy-pyridazine, N-oxide. (48%); mp, 84–87° C.

EXAMPLE 11

6-Oxo-1,6-dihydro-pyridazine-3-sulfonic Acid methyl-phenyl-amide

Step 1: 6-Methoxy-pyridazine-3-thiol.

A mixture of 3-chloro-6-methoxy-pyridazine (100 g), thiourea (105 g) and ethyl methyl ketone (1.8 L) was prepared and refluxed for three hours. The reaction mixture was then cooled and the supernatant was poured into water and extracted with 1M sodium hydroxide (4×100 mL). The sodium hydroxide solution was washed with ethyl acetate (2×50 mL) and the aqueous extract was acidified with sufficient concentrated hydrochloric acid to lower the pH to 5. The resulting yellow solid was collected and air dried to afford the title compound (24%, 23 g); mp, 198–200° C.

Step 2: 6-Methoxy-pyridazine-3-sulfonyl Fluoride

A mixture of 6-methoxy-pyridazine-3-thiol (7.1 g), methanol (100 mL), water (100 mL), and potassium hydrogen fluoride (39 g) was prepared and stirred at -10° C. for 30 minutes. Chlorine gas was bubbled into the mixture at a rate to ensure that the temperature did not exceed −10° C. The whitish-yellow reaction mixture was then poured into ice-cold water (50 mL) and the resulting white solid was filtered and air dried to afford the title compound (74%, 7.1 g); mp, 87–88° C.

Step 3: 6-Methoxy-pyridazine-3-sulfonic acid methyl-phenyl-amide

A mixture of 6-methoxy-pyridazine-3-sulfonyl fluoride (1.62 mmol, 312 mg) and N-methyl aniline (24.3 mmol, 0.26 mL) was prepared and heated at 100° C. for 12 hours. The mixture was then cooled. The resulting solid residue was purified by silica gel chromatography to isolate the title compound (53%, 240 mg); M+, 279.

Step 4: 6-Oxo-1,6-dihydro-pyridazine-3-sulfonic Acid methyl-phenyl-amide

A mixture of 6-methoxy-pyridazine-3-sulfonic acid methyl-phenyl-amide (239 mg), dioxane (4 mL) and concentrated hydrochloric acid (1 mL) was prepared and refluxed for one hour. The mixture was then evaporated to dryness. The resulting solid was triturated with water and the solid was collected to afford the title compound (75%, 171 mg); mp, 157–158° C.

EXAMPLE 12

6-Oxo-1,6-dihydro-pyridazine-3-sulfonic Acid isopropyl-phenyl-amide

The title compound was prepared according to a procedure analogous to that of Example 11 for 6-oxo-1,6-dihydro-pyridazine-3-sulfonic acid methyl-phenyl-amide, substituting N-isopropylaniline for N-methyl aniline in step 3, (20%); mp, 190–191° C.

EXAMPLE 13

6-Oxo-1,6-dihydro-pyridazine-3-sulfonic Acid (3,4-dichloro-phenyl)-methyl-amide

The title compound was prepared according to a procedure analogous to that of Example 11 for 6-oxo-1,6-dihydro-pyridazine-3-sulfonic acid methyl-phenyl-amide, substituting N-methyl-3,4-dichloroaniline for N-methylaniline (28%); mp, 207–208° C.

EXAMPLE 14

6-(4-Fluoro-phenylsulfanyl)-2H-pyridazin-3-one

A mixture of 3-(4-fluoro-phenylsulfanyl)-6-methoxy-pyridazine (250 mg), prepared by a procedure analogous to step 1 of Example 2, and concentrated hydrochloric acid was prepared and refluxed for 30 minutes. The mixture was then evaporated to dryness. The resulting residue was purified by silica gel chromatography (ethyl acetate as eluent) to afford the title compound (65%, 152 mg); mp, 99–101° C.

EXAMPLE 15

6-(Biphenyl-4-sulfonyl)-2H-pyridazin-3-one

Step 1: 3-(Biphenyl-4-sulfonyl)-6-methoxy-pyridazine

A mixture of 4-fluoro-benzene boronic acid (157 mg) 3-(4-fluoro-benzensulfonyl)-6-methoxy-pyridizine (247 mg), potassium carbonate (207 mg), Pd[P(Ph)$_3$]$_4$ (87 mg), toluene (4 mL), ethanol (2 mL) and water (1.5 mL) was prepared and refluxed for four hours. The mixture was cooled and water was added (10 mL). The mxture was then filtered and the resulting filtrate was extracted with ethyl acetate (20 mL). The ethyl acetate extract was washed with water and the ethyl acetate portion was collected and dried with anhydrous sodium sulfate and filtered. The filtrate was collected and evaporated to dryness to afford the title product of step 1. NMR δ 4.17 (s, 3H), 7.13 (m, 3H), 7.54 (m, 2H), 7.70 (m, 2H), 8.17 (m, 3H).

Step 2: 6-(Biphenyl-4-sulfonyl)-2H-pyridazin-3-one.

The product of step 1 was treated with concentrated hydrochloric acid accordin to step 3 of Example 1 to obtain the title compound. Mp. 219–220° C.

EXAMPLE 16

6-Benzyloxy-pyridazine-3-sulfonyl Fluoride

Step 1: 3-Benzyloxy-6-chloro-pyridazine.

Sodium metal (3.1 g) was added to benzyl alcohol (75 mL) and gently warmed to 50° C. for 30 minutes until all the sodium metal dissolved. A solution of 3,6-dichloropyridazine (135 mmol) in benzyl alcohol (75 mL) was added. The reaction mixture was kept at 100° C. for 24 hours. Excess benzyl alcohol was evaporated and the residue was extracted with ethyl acetate (3×100 mL) and the ethyl acetate extract was washed with water. The resulting ethyl acetate layer was collected, dried, filtered, and the filtrate was evaporated to afford the title compound (90%, 26.7 g); mp, 77–78° C.

Step 2: 6-Benzyloxy-pyridazine-3-thiol.

A mixture of 3-benzyloxy-6-chloro-pyridazine (4 g), thiourea (2.8 g) and ethyl methyl ketone (75 mL) was prepared and refluxed overnight. Excess ethyl methyl ketone was evaporated and the resulting residue was extracted with 2M sodium hydroxide (25 mL). The sodium hydroxide solution was then washed with ethyl acetate (2×30 mL). The aqueous layer was collected and sufficient concentrated hydrochloric acid was added to bring the pH to 5. The resulting solution was extracted with ethyl acetate (2×30 mL). The ethyl acetate extract was collected, dried, filtered, and the filtrate was evaporated to afford the title compound (15%, 605 mg); mp, 155–157° C.

Step 3: 6-Benzyloxy-pyridazine-3-sulfonyl Fluoride

A mixture of 6-benzyloxy-pyridazine-3-thiol (510 mg), methanol (10 mL), water (10 mL), and potassium hydrogen fluoride (1.83 g) was prepared and stirred at −10° C. for 30 minutes. Chlorine gas was bubbled into the mixture at a rate to ensure that the temperature not exceed −10° C. The resulting whitish-yellow reaction mixture was poured into ice cold water (50 mL) and the resulting white solid was filtered and air-dried to afford the title compound. (Yield 89%, 560 mg); mp, 85–86° C.

EXAMPLE 17

6-[2-(4-Chloro-phenyl)-2-oxo-ethanesulfonyl]-2H-pyridazin-3-one

Step 1: 1-(4-Chloro-phenyl)-2-(6-methoxy-pyridazin-3-ylsulfanyl)-ethanone.

A mixture of 2-mercapto-6-methoxy-pyridazine (10 mmol, 1.42 g), 4-chloro-α-bromo acetophenone (10 mmol, 2.33 g), potassium carbonate (20 mmol, 2.76 g), and dimethyl formamide (15 mL) was stirred at room temperature for one hour. The reaction mixture was filtered, the residue was washed with ethyl acetate (2×20 mL) and the combined filtrate was washed with water (2×20 mL). The ethyl acetate layer was collected, dried, filtered and the flitrate was evaporated to dryness to afford the title compound of step 1 (96%, 2.85 g); mass spectrum, m+295.

Step 2: 1-(4-Chloro-phenyl)-2-(6-methoxy-pyridazine-3-sulfonyl)-ethanone.

A mixture of the compound from step 1, (8.5 mmol, 2.3 g), MCPBA (25 mmol, 5.8 g), and methylene chloride (160 mL) was stirred at room temperature for 40 min. To the reaction mixture was added a saturated solution of sodium bi-carbonate (400 mL) and the methylene chloride layer was collected, dried, filtered and the filtrate was evaporated to afford the title compound of step 2 as a white solid (79%, 2.2 g); mp, 153–156° C.

Step 3: 6-[2-(4-Chloro-phenyl)-2-oxo-ethanesulfonyl]-2H-pyridazin-3-one

The compound from step 3 was transformed to the title compound, through acid hydrolysis, according to Step 3, of Example 1; (79%); mp, >240° C.

EXAMPLE 18

6-[2-(4-Chloro-phenyl)-2-hydroxy-ethanesulfonyl]-2H-pyridazin-3-one

A suspension was prepared of 6-[2-(4-chloro-phenyl)-2-oxo-ethanesulfonyl]-2H-pyridazin-3-one (1.0 mmol, 312 mg) prepared according to Example 17 in methanol (10 mL). Sodium borohydride (1.5 mmol, 55 mg) was added to the suspension at room temperature and stirred for 1 hour. The reaction mixture was evaporated and the residue was triturated with 10% hydrochloric acid (5 mL). The resulting white precipitate was filtered and air-dried to afford the title compound (69%, 218 mg); mp, 178–179° C.

EXAMPLE 19

Protocol for Determination of Aldose Reductase Inhibition

Test compound (TC) solutions were prepared by dissolving TC in 20 μl 20% dimethylsulfoxide (DMSO) and diluting with 100 mM potassium phosphate buffer, pH 7.0, to various TC concentrations, typically ranging from 5 mM to 1 μM. A "zero TC" solution was prepared that started with only 20 μl DMSO (no TC).

The assay for aldose reductase activity was performed in a 96-well plate. Initiation of the reaction (with substrate) was preceded by a 10 minute pre-incubation at 24° C. of 200 μl 100 mM potassium phosphate buffer, pH 7.0, containing 125 μM NADPH and 12.5 nM human recombinant Aldose Reductase (Wako Chemicals, Inc., #547-00581) with 25 μl TC solution. The reaction was initiated by the addition of 25 μl 20 mM D-glyceraldehyde (Sigma, St. Louis). The rate of decrease in $OD_{340}$ was monitored for 15 minutes at 24° C. in a 340 ATTC Plate Reader (SLT Lab Instruments, Austria). Inhibition by TC was measured as the percentage decrease in the rate of NADPH oxidation as compared to a non-TC containing sample.

What is claimed is:

1. A compound of formula I:

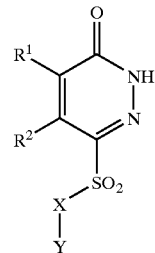

or a pharmaceutically acceptable salt of said compound, wherein,
$R^1$ and $R^2$ are independently hydrogen or methyl,
X is a covalent bond, $NR^3$ or CHR4, wherein,
$R^3$ is $(C_1-C_3)$alkyl or a phenyl that is optionally substituted with one or more substituents selected from OH, F, Cl, Br, I, CN, $CF_3$, $(C_1-C_6)$alkyl, O—$(C_1-C_6)$alkyl, $S(O)_n$—$(C_1-C_6)$alkyl and $SO_2$—$NR^6R^7$, and $R^4$ is hydrogen or methyl, and
Y is a phenyl or naphthyl ring optionally substituted with one or more substituents selected from Ar, OH, F, Cl, Br, I, CN, $CF_3$, $(C_1-C_6)$alkyl, O—$(C_1-C_6)$alkyl, $S(O)_n$—$(C_1-C_6)$alkyl and $SO_2$—$NR^6R^7$, or
X and Y together are $CH_2$—CH(OH)—Ar or $CH_2$—C(O)—Ar,
wherein,
Ar is a phenyl or naphthyl ring optionally substituted with one or more substituents selected from F, Cl, Br, I, CN, $CF_3$, $(C_1-C_6)$alkyl, O—$(C_1-C_6)$alkyl, $S(O)_n$—$(C_1-C_6)$alkyl and $SO_2$—$NR^6R^7$, n is independently for each occurrence 0, 1 or 2,
$R^6$ is independently for each occurrence H, $(C_1-C_6)$ alkyl, phenyl or naphthyl, and
$R^7$ is independently for each occurrence $(C_1-C_6)$alkyl, phenyl or naphthyl, with provisos that:
when X is a covalent bond, $R^1$ is hydrogen and $R^2$ is hydrogen, then Y is not an unsubstituted phenyl ring and Y is not a phenyl ring that is monosubstituted at the 4 position with methyl; and
when X is CHR4, $R^4$ is H, $R^1$ is hydrogen and $R^2$ is hydrogen, then Y is not an unsubstituted phenyl ring.

2. A compound of claim 1 wherein X is a covalent bond.

3. A compound of claim 2 wherein Y is a phenyl or naphthyl ring optionally substituted with one or more substituents selected from Ar, OH, F, Cl, Br, I, CN, $CF_3$, $(C_1-C_6)$alkyl, and O—$(C_1-C_6)$alkyl, wherein Ar is a phenyl or naphthyl ring optionally substituted with one or more substituents selected from F, Cl, Br, I, ON, $CF_3$, $(C_1C_6)$alkyl and O—$(C_1-C_6)$alkyl.

4. A compound of claim 3 wherein Y is a first phenyl or naphthyl ring optionally substituted with one or more substituents selected from Ar, OH, F, Cl, Br, $CF_3$, $(C_1-C_6)$alkyl, and O—$(_1-C_6)$alkyl, wherein Ar is a second phenyl or naphthyl ring optionally substituted with one or more substituents selected from F, Cl, Br, I, ON, $CF_3$, $(C_1-C_6)$alkyl and O—$(C_1-C_6)$alkyl, with proviso that said first phenyl or naphthyl ring is substituted with no more than one Ar.

5. A compound of claim 4 wherein Ar is a phenyl or naphthyl ring optionally substituted with one or more substituents selected from F and $CF_3$.

6. A compound of claim 2 wherein $R^1$ and $R^2$ are both hydrogen.

7. A compound of claim 3 wherein $R^1$ and $R^2$ are both hydrogen.

8. A compound of claim 4 wherein $R^1$ and $R^2$ are both hydrogen.

9. A compound of claim 5 wherein $R^1$ and $R^2$ are both hydrogen.

10. A compound of claim 9 selected from:
   6-(3-trifluoromethyl-benzenesulfonyl)-2H-pyridazin-3-one;
   6-(4-bromo-2—fluoro-benzenesulfonyl)-2H-pyridazin-3-one;
   6-(4-trifluoromethyl-benzenesulfonyl)-2H-pyridazin-3-one;
   6-(2—bromo-benzenesulfonyl)-2H-pyridazin-3-one;
   6-(3,4-dichloro-benzenesulfonyl)-2H-pyridazin-3-one;
   6-(4-methoxy-benzenesulfonyl)-2H-pyridazin-3-one;
   6-(3-bromo-benzenesulfonyl)-2H-pyridazin-3-one;
   6-(biphenyl-4-sulfonyl)-2H-pyridazin-3-one;
   6-(4'-fluoro-biphenyl-4-sulfonyl)-2H-pyridazin-3-one;
   6-(4'-trifluoromethyl-biphenyl-4-sulfonyl)-2H-pyridazin-3-one;
   6-(3',5'-bis-trifluoromethyl-biphenyl-4-sulfonyl)-2H-pyridazin-3-one;
   6-(biphenyl-2-sulfonyl)-2H-pyridazin-3-one;
   6-(4'-trifluoromethyl-biphenyl-2-sulfonyl)-2H-pyridazin-3-one;
   6-(2—hydroxy-benzenesulfonyl)-2H-pyridazin-3-one;
   6-(2—chloro-benzenesulfonyl)-2H-pyridazin-3-one;
   6-(3-chloro-benzenesulfonyl)-2H-pyridazin-3-one;
   6-(2,3-dichloro-benzenesulfonyl)-2H-pyridazin-3-one;
   6-(2,5-dichloro-benzenesulfonyl)-2H-pyridazin-3-one;
   6-(4-fluoro-benzenesulfonyl)-2H-pyridazin-3-one;
   6-(4-chloro-benzenesulfonyl)-2H-pyridazin-3-one;
   6-(2—fluoro-benzenesulfonyl)-2H-pyridazin-3-one;
   6-(2,3-difluoro-benzenesulfonyl)-2H-pyridazin-3-one;
   6-(2,4-dichloro-benzenesulfonyl)-2H-pyridazin-3-one;
   6-(2,4-difluoro-benzenesulfonyl)-2H-pyridazin-3-one;
   6-(2,6-dichloro-benzenesulfonyl)-2H-pyridazin-3-one;
   6-(2—chloro-4-fluoro-benzenesulfonyl)-2H-pyridazin-3-one;
   6-(2—bromo-4-fluoro-benzenesulfonyl)-2H-pyridazin-3-one; and
   6-(naphthalene-1-sulfonyl)-2H-pyridazin-3-one.

11. A compound of claim 10 selected from:
   6-(2—chloro-benzenesulfonyl)-2H-pyridazin-3-one;
   6-(3-chloro-benzenesulfonyl)-2H-pyridazin-3-one;
   6-(2,3-dichloro-benzenesulfonyl)-2H-pyridazin-3-one;
   6-(2,5-dichloro-benzenesulfonyl)-2H-pyridazin-3-one;
   6-(4-fluoro-benzenesulfonyl)-2H-pyridazin-3-one;
   6-(4-chloro-benzenesulfonyl)-2H-pyridazin-3-one;
   6-(2—fluoro-benzenesulfonyl)-2H-pyridazin-3-one;
   6-(2,3-difluoro-benzenesulfonyl)-2H-pyridazin-3-one;
   6-(2,4-dichloro-benzenesulfonyl)-2H-pyridazin-3-one;
   6-(2,4-difluoro-benzenesulfonyl)-2H-pyridazin-3-one;
   6-(2,6-dichloro-benzenesulfonyl)-2H-pyridazin-3-one;
   6-(2—chloro-4-fluoro-benzenesulfonyl)-2H-pyridazin-3-one;
   6-(2—bromo-4-fluoro-benzenesulfonyl)-2H-pyridazin-3-one; and
   6-(naphthalene-1-sulfonyl)-2H-pyridazin-3-one.

12. A compound of claim 11 selected from:
   6-(2—chloro-benzenesulfonyl)-2H-pyridazin-3-one;
   6-(3-chloro-benzenesulfonyl)-2H-pyridazin-3-one;
   6-(2,3-dichloro-benzenesulfonyl)-2H-pyridazin-3-one;
   6-(2,5-dichloro-benzenesulfonyl)-2H-pyridazin-3-one;
   6-(2,3-difluoro-benzenesulfonyl)-2H-pyridazin-3-one;
   6-(2,4-dichloro-benzenesulfonyl)-2H-pyridazin-3-one;
   6-(2,4-difluoro-benzenesulfonyl)-2H-pyridazin-3-one;
   6-(2,6-dichloro-benzenesulfonyl)-2H-pyridazin-3-one;
   6-(2—chloro-4-fluoro-benzenesulfonyl)-2H-pyridazin-3-one;
   6-(2—bromo-4-fluoro-benzenesulfonyl)-2H-pyridazin-3-one; and
   6-(naphthalene-1-sulfonyl)-2H-pyridazin-3-one.

13. A compound of claim 12 selected from:
   6-(2,3-difluoro-benzenesulfonyl)-2H-pyridazin-3-one;
   6-(2,4-dichloro-benzenesulfonyl)-2H-pyridazin-3-one;
   6-(2—bromo-4-fluoro-benzenesulfonyl)-2H-pyridazin-3-one; and
   6-(naphthalene-1-sulfonyl)-2H-pyridazin-3-one.

14. A compound of claim 1 wherein X is $CHR^4$ wherein $R^4$ is hydrogen or methyl.

15. A compound of claim 14 wherein Y is a phenyl or naphthyl ring optionally substituted with one or more substituents selected from Ar, OH, F, Cl, Br, I, CN, $CF_3$, $(C_1–C_6)$alkyl, and O—$(C_1–C_6)$alkyl, wherein Ar is a phenyl or naphthyl ring optionally substituted with one or more substituents selected from F, Cl, Br, I, CN, $CF_3$, $(C_1–C_6)$alkyl and O—$(C_1–C_6)$alkyl.

16. A compound of claim 15 wherein Y is a phenyl or naphthyl ring optionally substituted with one or more substituents selected from F, Cl, Br, $CF_3$, $(C_1–C_6)$alkyl, and O—$(C_1–C_6)$alkyl.

17. A compound of claim 14 wherein $R^1$ and $R^2$ are both hydrogen.

18. A compound of claim 15 wherein $R^1$ and $R^2$ are both hydrogen.

19. A compound of claim 16 wherein $R^1$ and $R^2$ are both hydrogen.

20. A compound of claim 19 selected from:
   6-(4-bromo-2-fluoro-phenylmethanesulfonyl)-2H-pyridazin-3-one;
   6-(2,6-dichloro-phenylmethanesulfonyl)-2H-pyridazin-3-one;
   6-(2—methoxy-phenylmethanesulfonyl)-2H-pyridazin-3-one;
   6-(2—fluoro-phenylmethanesulfonyl)-2H-pyridazin-3-one;
   6-(4-chloro-2-fluoro-phenylmethanesulfonyl)-2H-pyridazin-3-one;
   6-(2,3,4-trifluoro-phenylmethanesulfonyl)-2H-pyridazin-3-one;
   6-(2,4,6-trifluoro-phenylmethanesulfonyl)-2H-pyridazin-3-one;
   6-(2—fluoro-3-methyl-phenylmethanesulfonyl)-2H-pyridazin-3-one;
   6-(3-trifluoromethyl-phenylmethanesulfonyl)-2H-pyridazin-3-one;
   6-(2,3-dichloro-phenylmethanesulfonyl)-2H-pyridazin-3-one;
   6-(2—trifluoromethyl-phenylmethanesulfonyl)-2H-pyridazin-3-one;

6-(2—fluoro-3-trifluoromethyl-phenylmethanesulfonyl)-2H-pyridazin-3-one;

6-(2—chloro-6-fluoro-phenylmethanesulfonyl)-2H-pyridazin-3-one;

6-(2,3-dichloro-phenylmethanesulfonyl)-2H-pyridazin-3-one;

6-(1-phenyl-ethanesulfonyl)-2H-pyridazin-3-one;

6-[1-(3-trifluoromethyl-phenyl)-ethanesulfonyl]-2H-pyridazin-3-one;

6-[1-(2—trifluoromethyl-phenyl)-ethanesulfonyl]-2H-pyridazin-3-one; and

6-[1-(2,4-dichloro-phenyl)-ethanesulfonyl]-2H-pyridazin-3-one.

21. A compound of claim 1 wherein X is $NR^3$, wherein $R^3$ is $(C_1-C_3)$alkyl or a phenyl that is optionally substituted with one or more substituents selected from OH, F, Cl, Br, I, CN, $CF_3$, $(C_1-C_6)$alkyl, O—$(C_1-C_6)$alkyl, $S(O)_n$—$(C_1-C_6)$alkyl and $SO_2$—$NR^6R^7$.

22. A compound of claim 21 wherein Y is a phenyl or naphthyl ring optionally substituted with one or more substituents selected from Ar, OH, F, Cl, Br, I, CN, $CF_3$, $(C_1-C_6)$alkyl, and O—$(C_1-C_6)$alkyl, wherein Ar is a phenyl or naphthyl ring optionally substituted with one or more substituents selected from F, Cl, Br, I, CN, $CF_3$, $(C_1-C_6)$alkyl and O—$(C_1-C_6)$alkyl.

23. A compound of claim 21 wherein $R^1$ and $R^2$ are both hydrogen.

24. A compound of claim 22 wherein $R^1$ and $R^2$ are both hydrogen.

25. A compound of claim 24 selected from:

6-oxo-1,6-dihydro-pyridazine-3-sulfonic acid methyl-phenyl-amide;

6-oxo-1,6-dihydro-pyridazine-3-sulfonic acid isopropyl-phenyl-amide; and 6-oxo-1,6-dihydro-pyridazine-3-sulfonic acid (3,4-dichloro-phenyl)-methyl-amide.

26. A compound of claim 1 wherein $R^1$ and $R^2$ are both hydrogen and X and Y together are $CH_2$—CH(OH)—Ar or $CH_2$—C(O)—Ar.

27. A compound of claim 26 wherein X and Y together are $CH_2$—CH(OH)—Ar" or $CH_2$—C(O)—Ar" wherein Ar" is 4-chlorophenyl.

28. A compound of formula XI:

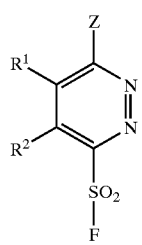

XI wherein:

$R^1$ and $R^2$ are independently hydrogen or methyl and Z is O—$(C_1-C_6)$alkyl, O—Ar, or O—$CH_2$—Ar', wherein Ar' is a phenyl ring that is optionally substituted with one or more substituents selected from a halogen, a $(C_1-C_3)$alkyl and a O—$(C_1-C_3)$alkyl.

29. A compound of claim 28 wherein $R^1$ and $R^2$ are both hydrogen and Z is methoxy or benzyloxy.

30. A pharmaceutical composition comprising a compound of formula I:

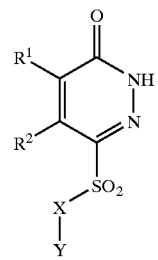

I wherein, $R^1$ and $R^2$ are independently hydrogen or methyl,

X is a covalent bond, $NR^3$ or CHR4, wherein, $R^3$ is $(C_1-C_3)$alkyl or a phenyl that is optionally substituted with one or more substituents selected from OH, F, Cl, Br, I, CN, $CF_3$, $(C_1-C_6)$alkyl, O—$(C_1-C_6)$alkyl, $S(O)_n$—$(C_1-C_6)$alkyl and $SO_2$—$NR^6R^7$, and $R^4$ is hydrogen or methyl, and Y is a phenyl or naphthyl ring optionally substituted with one or more substituents selected from Ar, OH, F, Cl, Br, I, CN, $CF_3$, $(C_1-C_6)$alkyl, O—$(C_1-C_6)$alkyl, $S(O)_n$—$(C_1-C_6)$alkyl and $SO_2$—$_{NR}{}^6R^7$, or X and Y together are $CH_2$—CH(OH)—Ar or $CH_2$—C(O)—Ar, wherein, Ar is a phenyl or naphthyl ring optionally substituted with one or more substituents selected from F, Cl, Br, I, CN, $CF_3$, $(C_1-C_6)$alkyl, O—$(C_1-C_6)$alkyl, $S(O)_n$—$(C_1-C_6)$alkyl and $SO_2$—$NR^6R^7$, n is independently for each occurrence 0, 1 or 2, $R^6$ is independently for each occurrence H, $(C_1-C_6)$alkyl, phenyl or naphthyl, and $R^7$ is independently for each occurrence $(C_1-C_6)$alkyl, phenyl or naphthyl, or a pharmaceutically acceptable salt of said compound, and a pharmaceutically acceptable vehicle, diluent or carrier.

31. A pharmaceutical composition of claim 30 wherein said compound of formula I, or a pharmaceutically acceptable salt of said compound, is of an amount effective in inhibiting the enzyme aldose reductase in a mammal affected by diabetes.

32. A pharmaceutical composition of claim 31 wherein said mammal is a human.

33. A pharmaceutical composition comprising a first compound of formula I:

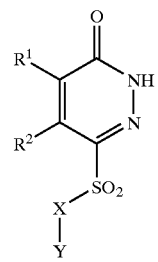

I wherein, $R^1$ and $R^2$ are independently hydrogen or methyl,

X is a covalent bond, $NR^3$ or CHR4, wherein, $R^3$ is $(C_1-C_3)$alkyl or a phenyl that is optionally substituted with one or more substituents selected from OH, F, Cl, Br, I, CN, CF$_3$, (C$_1$–C$_6$)alkyl, O—(C$_1$–C$_6$)alkyl, S(O)$_n$—(C$_1$–C$_6$)alkyl and SO2—NR$^6$R$^7$, and R$^4$ is hydrogen or methyl, and Y is a phenyl or naphthyl ring optionally substituted with one or more substituents selected from Ar, OH, F, Cl, Br, I, CN, CF$_3$, (C$_1$–C$_6$)alkyl, O—(C$_1$–C$_6$)alkyl, S(O)$_n$—(C$_1$–C$_6$)alkyl and SO$_2$—NR$^6$R$^7$, or X and Y together are CH$_2$—CH(OH)—Ar or CH$_2$—C(O)—Ar, wherein, Ar is a phenyl or naphthyl ring optionally substituted with one or more substituents selected from F, Cl, Br, I, CN, CF$_3$, (C$_1$–C$_6$)alkyl, O—(C$_1$–C$_6$)alkyl, S(O)$_n$—(C$_1$–C$_6$)alkyl and SO$_2$—NR$^6$R$^7$, n is independently for each occurrence 0, 1 or 2, R$^6$ is independently for each occurrence H, (C$_1$–C$_6$)alkyl, phenyl or naphthyl, and R$^7$ is independently for each occurrence (C$_1$–C$_6$)alkyl, phenyl or naphthyl, or a pharmaceutically acceptable salt of said first compound, and a second compound selected from:
a sorbitol dehydrogenase inhibitor;
a selective serotonin reuptake inhibitor;
a 3-hydroxy-3-methylglutaryl coenzyme A reductase inhibitor;
an angiotensin converting enzyme inhibitor;
a glycogen phosphorylase inhibitor;
an angiotensin II receptor antagonist;
a γ-aminobutyric acid (GABA) agonist;
a phosphodiesterase type 5 inhibitor,
and a pharmaceutically acceptable salt of said second compound.

34. A pharmaceutical composition of claim 33 wherein said second compound comprises a sorbitol dehydrogenase inhibitor, or a pharmaceutically acceptable salt of said second compound.

35. A pharmaceutical composition of claim 33 wherein said second compound comprises a selective serotonin reuptake inhibitor, or a pharmaceutically acceptable salt of said second compound.

36. A pharmaceutical composition of claim 33 wherein said second compound comprises a 3-hydroxy-3-methylglutaryl coenzyme A reductase inhibitor, or a pharmaceutically acceptable salt of said second compound.

37. A pharmaceutical composition of claim 33 wherein said second compound comprises an angiotensin converting enzyme inhibitor, or a pharmaceutically acceptable salt of said second compound.

38. A pharmaceutical composition of claim 33 wherein said second compound comprises a glycogen phosphorylase inhibitor or a pharmaceutically acceptable salt of said second compound.

39. A pharmaceutical composition of claim 33 wherein said second compound comprises an angiotensin II receptor antagonist, or a pharmaceutically acceptable salt of said second compound.

40. A pharmaceutical composition of claim 33 wherein said second compound comprises a γ-aminobutyric acid agonist, or a pharmaceutically acceptable salt of said second compound.

41. A pharmaceutical composition of claim 33 wherein said second compound comprises a phosphodiesterase type 5 inhibitor, or a pharmaceutically acceptable salt of said second compound.

42. A therapeutic method comprising administering to a mammal in need of treatment or prevention of diabetic complications, an aldose reductase inhibiting amount of a compound of formula I:

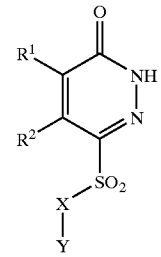

wherein,

R$^1$ and R$^2$ are independently hydrogen or methyl,

X is a covalent bond, NR$^3$ or CHR4, wherein,

R$^3$ is (C$_1$–C$_3$)alkyl or a phenyl that is optionally substituted with one or more substituents selected from OH, F, Cl, Br, I, CN, CF$_3$, (C$_1$–C$_6$)alkyl, O—(C$_1$–C$_6$)alkyl, S(O)$_n$—(C$_1$–C$_6$)alkyl and SO$_2$—NR$^6$R$^7$, and R$^4$ is hydrogen or methyl, and Y is a phenyl or naphthyl ring optionally substituted with one or more substituents selected from Ar, OH, F, Cl, Br, I, CN, CF$_3$, (C$_1$–C$_6$)alkyl, O—(C$_1$–C$_6$)alkyl, S(O)$_n$—(C$_1$–C$_6$)alkyl and SO$_2$—NR$^6$R$^7$, or X and Y together are CH$_2$—CH(OH)—Ar or CH$_2$—C(O)—Ar, wherein, Ar is a phenyl or naphthyl ring optionally substituted with one or more substituents selected from F, Cl, Br, I, CN, CF$_3$, (C$_1$–C$_6$)alkyl, O—(C$_1$–C$_6$)alkyl, S(O)$_n$—(C$_1$–C$_6$)alkyl and SO$_2$—NR$^6$R$^7$, n is independently for each occurrence 0, 1 or 2, R$^6$ is independently for each occurrence H, (C$_1$–C$_6$)alkyl, phenyl or naphthyl, and R$^7$ is independently for each occurrence (C$_1$–C$_6$)alkyl, phenyl or naphthyl, or a pharmaceutically acceptable salt of said compound.

43. A therapeutic method of claim 42 wherein said mammal is a human.

44. A therapeutic method comprising administering to a mammal in need of treatment or prevention of diabetic complications an aldose reductase inhibiting amount of a first compound of formula I:

wherein,

R$^1$ and R$^2$ are independently hydrogen or methyl,

X is a covalent bond, NR$^3$ or CHR4, wherein,

R$^3$ is (C$_1$–C$_3$)alkyl or a phenyl that is optionally substituted with one or more substituents selected from OH, F, Cl, Br, I, CN, CF$_3$, (C$_1$–C$_6$)alkyl, O—(C$_1$–C$_6$)alkyl, S(O)$_n$—(C$_1$–C$_6$)alkyl and SO$_2$—NR$^6$R$^7$, and R$^4$ is hydrogen or methyl, and Y is a phenyl or naphthyl ring optionally substituted with one or more substituents selected from Ar, OH, F, Cl, Br, I, CN, CF$_3$, (C$_1$–C$_6$)alkyl, O—(C$_1$–C$_6$)alkyl, S(O)$_n$—(C$_1$–C$_6$)alkyl and SO$_2$—NR$^6$R$^7$, or X and Y together are CH$_2$—CH(OH)—Ar or CH$_2$—C(O)—Ar, wherein, Ar is a phenyl or naphthyl ring optionally substituted with one or more substituents selected from F, Cl, Br, I, CN, CF$_3$, (C$_1$–C$_6$)alkyl, O—(C$_1$–C$_6$)alkyl, S(O)$_n$—(C$_1$–C$_6$)alkyl and SO$_2$—NR$^6$R$^7$, n is independently for each occurrence 0, 1 or 2, R$^6$ is independently for each occurrence H, (C$_1$–C$_6$)alkyl, phenyl or naphthyl, and R[7] is independently for each occurrence (C₁–C₆)alkyl, phenyl or naphthyl, and a pharmaceutically acceptable salt of said first compound, and a second compound selected from:
  a sorbitol dehydrogenase inhibitor;
  a selective serotonin reuptake inhibitor;
  a 3-hydroxy-3-methylglutaryl coenzyme A reductase inhibitor;
  an angiotensin converting enzyme inhibitor;
  a glycogen phosphorylase inhibitor;
  an angiotensin II receptor antagonist;
  a γ-aminobutyric acid (GABA) agonist;
  a phosphodiesterase type 5 inhibitor, and a pharmaceutically acceptable salt of said second compound.

45. A therapeutic method of claim 44 wherein said second compound is a sorbitol dehydrogenase inhibitor and wherein said second compound is administered in a sorbitol dehydrogenase inhibiting amount.

46. A therapeutic method of claim 44 wherein said second compound is a selective serotonin reuptake inhibitor and wherein said second compound is administered in a selective serotonin reuptake inhibiting amount.

47. A therapeutic method of claim 44 wherein said second compound is a 3-hydroxy-3-methylglutaryl coenzyme A reductase inhibitor and wherein said second compound is administered in a hydroxy-3-methylglutaryl coenzyme A reductase inhibiting amount.

48. A therapeutic method of claim 44 wherein said second compound is an angiotensin converting enzyme inhibitor and wherein said second compound is administered in an angiotensin converting enzyme inhibiting amount.

49. A therapeutic method of claim 44 wherein said second compound is a glycogen phosphorylase inhibitor and wherein said second compound is administered in a glycogen phosphorylase inhibiting amount.

50. A therapeutic method of claim 44 wherein said second compound is an angiotensin II receptor antagonist and wherein said second compound is administered in an angiotensin II receptor blocking amount.

51. A therapeutic method of claim 44 wherein said second compound is a γ-aminobutyric acid agonist and wherein said second compound is administered in a γ-aminobutyric acid receptor binding amount.

52. A therapeutic method of claim 44 wherein said second compound is a phosphodiesterase type 5 inhibitor and wherein said second compound is administered in a phosphodiesterase type 5 inhibiting amount.

53. A therapeutic method of claim 44 wherein said mammal is a human.

54. A process for preparing a compound of formula XII:

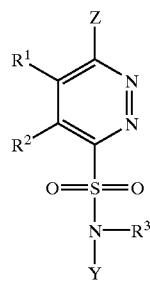

XII comprising reacting a compound of claim 53 with HN(R³)—Y to form a compound of formula XII, wherein:

Y is a phenyl or naphthyl ring optionally substituted with one or more substituents selected from Ar, OH, F, Cl, Br, I, CN, CF₃, (C₁–C₆)alkyl, O—(C₁–C₆)alkyl, S(O)ₙ—(C₁–C₆)alkyl and SO₂—NR⁶R⁷, wherein Ar is a phenyl or naphthyl ring optionally substituted with one or more substituents selected from F, Cl, Br, I, CN, CF₃, (C₁–C₆)alkyl, O—(C₁–C₆)alkyl, S(O)ₙ—(C₁–C₆)alkyl and SO₂—NR⁶R⁷, n is independently for each occurrence 0, 1 or 2, R⁶ is independently for each occurrence H, (C₁–C₆)alkyl, phenyl or naphthyl, and R⁷ is independently for each occurrence (C₁–C₆)alkyl, phenyl or naphthyl;

Z is O—(C₁–C₆)alkyl, O—Ar', or O—CH₂—Ar', wherein Ar' is a phenyl ring that is optionally substituted with one or more substituents selected from a halogen and a (C₁–C₃)alkyl;

R¹ and R² are independently hydrogen or methyl; and

R³ is (C₁–C₃)alkyl or a phenyl that is optionally substituted with one or more substituents selected from OH, F, Cl, Br, I, CN, CF₃, (C₁–C₆)alkyl, O—(C₁–C₆)alkyl, S(O)ₙ—(C₁–C₆)alkyl and SO₂—N R⁶R⁷.

55. A process for preparing a compound of formula XIII:

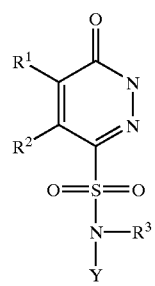

XIII comprising hydrolyzing a compound of formula XII prepared by a method of claim 53 with a mineral acid to form a compound of formula XIII, wherein:

Y is a phenyl or naphthyl ring optionally substituted with one or more substituents selected from Ar, OH, F, Cl, Br, I, CN, CF₃, (C₁–C₆)alkyl, O—(C₁–C₆)alkyl, S(O)ₙ—(C₁–C₆)alkyl and SO₂—NR⁶R⁷, wherein Ar is a phenyl or naphthyl ring optionally substituted with one or more substituents selected from F, Cl, Br, I, CN, CF₃, (C₁–C₆)alkyl, O—(C₁–C₆)alkyl, S(O)ₙ—(C₁–C₆)alkyl and SO₂—NR⁶R⁷, n is independently for each occurrence 0, 1 or 2, R⁶ is independently for each occurrence H, (C₁–C₆)alkyl, phenyl or naphthyl, and R⁷ is independently for each occurrence (C₁–C₆)alkyl, phenyl or naphthyl;

R¹ and R² are independently hydrogen or methyl; and

R³ is (C₁–C₃)alkyl or a phenyl that is optionally substituted with one or more substituents selected from OH, F, Cl, Br, I, CN, CF₃, (C₁–C₆)alkyl, O—(C₁–C₆)alkyl, S(O)ₙ—(C₁–C₆)alkyl and SO₂—NR⁶R⁷.

56. A kit comprising:

a first dosage form comprising a compound of formula I:

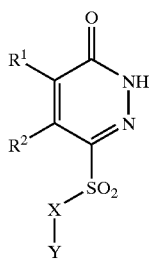

wherein, $R^1$ and $R^2$ are independently hydrogen or methyl,

X is a covalent bond, $NR^3$ or CHR4, wherein, $R^3$ is $(C_1-C_3)$alkyl or a phenyl that is optionally substituted with one or more substituents selected from OH, F, Cl, Br, I, CN, $CF_3$, $(C_1-C_6)$alkyl, O—$(C_1-C_6)$alkyl, $S(O)_n$—$(C_1-C_6)$alkyl and $SO_2$—$NR^6R^7$, and $R^4$ is hydrogen or methyl, and Y is a phenyl or naphthyl ring optionally substituted with one or more substituents selected from Ar, OH, F, Cl, Br, I, CN, $CF_3$, $(C_1-C_6)$alkyl, O—$(C_1-C_6)$alkyl, $S(O)_n$—$(C_1-C_6)$alkyl and $SO_2$—$NR^6R^7$, or X and Y together are $CH_2$—CH(OH)—Ar or $CH_2$—C(O)—Ar, wherein, Ar is a phenyl or naphthyl ring optionally substituted with one or more substituents selected from F, Cl, Br, I, CN, $CF_3$, $(C_1-C_6)$alkyl, O—$(C_1-C_6)$alkyl, $S(O)_n$—$(C_1-C_6)$alkyl and $SO_2$—$NR^6R^7$, n is independently for each occurrence 0, 1 or 2, $R^6$ is independently for each occurrence H, $(C_1-C_6)$alkyl, phenyl or naphthyl, and $R^7$ is independently for each occurrence $(C_1-C_6)$alkyl, phenyl or naphthyl, or a pharmaceutically acceptable salt of said compound;

a second dosage form comprising a second compound selected from:

a sorbitol dehydrogenase inhibitor;

a selective serotonin reuptake inhibitor;

a 3-hydroxy-3-methylglutaryl coenzyme A reductase inhibitor;

an angiotensin converting enzyme inhibitor;

a glycogen phosphorylase inhibitor;

an angiotensin II receptor antagonist;

a γ-aminobutyric acid (GABA) agonist;

a phosphodiesterase type 5 inhibitor, and a pharmaceutically acceptable salt of said compound; and a container.

* * * * *